US011576888B2

(12) United States Patent
Marchetti et al.

(10) Patent No.: US 11,576,888 B2
(45) Date of Patent: Feb. 14, 2023

(54) METHODS FOR TREATING CARDIOVASCULAR DISEASES

(71) Applicant: OLATEC THERAPEUTICS LLC, New York, NY (US)

(72) Inventors: Carlo Marchetti, Denver, CO (US); Charles A. Dinarello, Boulder, CO (US)

(73) Assignee: OLATEC THERAPEUTICS LLC, New York, NY (US)

(*) Notice: Subject to any disclaimer, the term of this patent is extended or adjusted under 35 U.S.C. 154(b) by 44 days.

(21) Appl. No.: 16/452,189

(22) Filed: Jun. 25, 2019

(65) Prior Publication Data
US 2019/0307718 A1 Oct. 10, 2019

Related U.S. Application Data

(63) Continuation of application No. PCT/US2018/012625, filed on Jan. 5, 2018.

(60) Provisional application No. 62/443,387, filed on Jan. 6, 2017, provisional application No. 62/506,843, filed on May 16, 2017.

(51) Int. Cl.
| | |
|---|---|
| A61K 31/275 | (2006.01) |
| A61K 9/00 | (2006.01) |
| A61P 9/10 | (2006.01) |
| A61P 9/04 | (2006.01) |
| A61K 9/48 | (2006.01) |

(52) U.S. Cl.
CPC ......... *A61K 31/275* (2013.01); *A61K 9/0019* (2013.01); *A61K 9/0053* (2013.01); *A61K 9/4866* (2013.01); *A61P 9/04* (2018.01); *A61P 9/10* (2018.01)

(58) Field of Classification Search
CPC .. A61K 31/275; A61K 9/0019; A61K 9/0053; A61K 9/4866; A61P 9/04; A61P 9/10; C12Q 1/6886; C12Q 2600/106; C12Q 2600/158; C12Q 2600/178; G16B 20/00; G16B 25/00; G16B 5/00; G16H 50/20; G16H 50/30
USPC ........................................................ 514/279
See application file for complete search history.

(56) References Cited

U.S. PATENT DOCUMENTS

| | | | | |
|---|---|---|---|---|
| 8,476,316 B2* | 7/2013 | St. Laurent | .......... | A61K 9/0053 |
| | | | | 514/526 |
| 8,829,046 B2* | 9/2014 | St. Laurent | .......... | A61K 9/0014 |
| | | | | 514/526 |
| 8,975,297 B2* | 3/2015 | St. Laurent | ............. | A61P 25/04 |
| | | | | 514/526 |
| 9,492,420 B2* | 11/2016 | St. Laurent | .......... | A61K 9/0014 |
| 2012/0157524 A1 | 6/2012 | St. Laurent | | |
| 2013/0324603 A1 | 12/2013 | St. Laurent et al. | | |

OTHER PUBLICATIONS

Toldo et al. (Circulation, Issue: vol. 132(Suppl_3) Supplements, Nov. 10, 2015, p. A15506).*
Ajdukovic, Jasna (J Clin Exp Cardiolog, The Role of NLRP3 Inflammasome in Cardiovascular Diseases2015, 6:9 DOI: 10.4172/2155-9880.1000399).*
Toldo S et al. (Inhibition of the NLRP3 inflammasome limits the inflammatory injury folloEpub Feb. 4, 2016. PMID: 26896627).*
Stefano Toldo et al. (Antioxidants & Redox Signaling, vol. 22, No. 13; Published Online: Apr. 15, 2015—https://doi.org/10.1089/ars.2014.598; Forum Review Articles, the Inflammasome in Myocardial Injury and Cardiac Remodeling.*
Skouras, Damaris "Damaris Skouras—CEO of Olatec on Treating Inflammation" OneMedMarket News & Information Center, Dec. 23, 2016. p. 1-4.
Lee, J-Y et al. "Cyclic AMP prolongs graft survival by suppressing apoptosis and inflammatory gene expression in acute cardiac allograft rejection" Experimental and Molecular Medicine; Jan. 2010, vol. 42, No. 1, pp. 69-79.
Jie-Young Lee, et al., "Cyclic AMP prolongs graft survival by suppressing apoptosis and inflammatory gene expression in acute cardiac allograft rejection", Experimental and Molecular Medicine, Jan. 2010, vol. 42, No. 1, pp. 69-79.
Carlo Marchetti, et al., "Pharmacologic inhibition of the NLRP3 inflammasome preserves cardiac function after ischemic and non-ischemic injury in the mouse", Journal of Cardiovascular Pharmacology, Jul. 2015, vol. 66, No. 1, pp. 1-8.
Matthias Pauschinger, et al., "Carvedilol improves left ventricular function in murine coxsackievirus-induced acute myocarditis Association with reduced myocardial interleukin-1β and MMP-8 expression and a modulated immune response". The European Journal of Heart Failure, 2005, vol. 7, pp. 444-452.
International Search Report dated Mar. 7, 2018 issued in PCT/US18/12625, (One page).

* cited by examiner

*Primary Examiner* — Sarah Pihonak
(74) *Attorney, Agent, or Firm* — Perkins Coie LLP; Viola Kung

(57) ABSTRACT

The present invention is directed to a method for treating cardiovascular diseases such as acute myocardial infarction, atherosclerosis, heart failure, stroke, thrombosis, carditis (including acute myocarditis, acute pericarditis and complicated pericarditis), cardiac allograft rejection, cardiomyopathy, and peripheral vascular diseases. The method comprises administering to a subject in need thereof dapansutrile, in an effective amount. A preferred route of administration is oral administration.

7 Claims, 8 Drawing Sheets

Relative to vehicle control group (Group 1): *** p < 0.001

Relative to vehicle control group (Group 1): *** p < 0.001

Relative to vehicle control group (Group 1): * $p < 0.001$;  $p < 0.01$; * $p < 0.05$ Relative to vehicle control group (Group 1): * $p < 0.001$;  $p < 0.01$

METHODS FOR TREATING CARDIOVASCULAR DISEASES

This application is a continuation of PCT/US2018/012625, filed Jan. 5, 2018; which claims the benefit of U.S. Provisional Application Nos. 62/506,843, filed May 16, 2017, and 62/443,387, filed Jan. 6, 2017. The contents of the above-identified applications are incorporated herein by reference in their entirety.

FIELD OF THE INVENTION

The present invention relates to methods for treating cardiovascular diseases such acute myocardial infarction (AMI), atherosclerosis, heart failure (HF), stroke, thrombosis, carditis (including acute myocarditis, acute pericarditis and complicated pericarditis), cardiac allograft rejection, cardiomyopathy, and peripheral vascular diseases, by administering an effective amount of dapansutrile.

BACKGROUND OF THE INVENTION

Acute myocardial infarction (AMI) is a major cause of morbidity and mortality worldwide. AMI is caused by sudden onset of myocardial ischemia and ensuing necrosis. AMI survivors remain at high risk of death in the years after the event. The most common complication of AMI is the occurrence of left ventricular (LV) dysfunction and heart failure. The initial ischemic damage to the myocardium activates a cascade of events that eventually lead to adverse cardiac remodeling and heart failure with ensuing excesses in morbidity and mortality. Interleukin-1 (IL-1) receptor antagonist (IL-1Ra), a member of the IL-1 family, is a naturally occurring anti-inflammatory protein that behaves as an acute phase reactant Like other acute-phase reactants, IL-1Ra levels increase during AMI, and its levels correlate with prognosis. (Abbate et al, *Circulation,* 117: 2670-2683, 2008)

Atherosclerosis is the underlying disease process responsible for vascular conditions that causes the death of over one third of the population of the Western world. It is a chronic inflammatory response in the walls of arteries, in large part due to the accumulation of macrophage white blood cells and promoted by low density lipoproteins without adequate removal of fats and cholesterol from the macrophages by functional high density lipoproteins (HDL). It is caused by the formation of multiple plaques within the arteries, resulting in a hardening of the arteries. As the disease progresses, there is a migration of the endothelial cells over the ensuing plaques. These plaques are composed of cholesterol, activated platelets, macrophages and accumulated lipoproteins. The combination of these plaques, inflammation and endothelial cell migration leads to this hardening the arteries and loss elasticity of the vessels.

Heart failure (HF) occurs when the heart muscle is weakened and cannot pump enough blood to meet the body's needs for blood and oxygen.

Myocarditis is an inflammatory disease of the heart muscle (myocardium) that can result from a variety of causes. Whilemost cases are produced by a viral infection, an inflammation of the heart muscle may also be instigated by toxins, drugs, and hypersensitive immune reactions. Acute myocarditis is an inflammatory disorder of the heart muscle in which the severity of injury depends both on the nature of the offending agent (i.e., virus) and on the ensuing inflammation.

Pericarditis is inflammation of the pericardium (the fibrous sac surrounding the heart). Symptoms typically include sudden onset of sharp chest pain.

Stroke is when poor blood flow to the brain results in cell death. There are two main types of stroke: ischemic, due to lack of blood flow, and hemorrhagic, due to bleeding. They result in part of the brain not functioning properly. Signs and symptoms of a stroke may include an inability to move or feel on one side of the body, problems understanding or speaking, feeling like the world is spinning, or loss of vision to one side among other signs and symptoms.

STEMI is a common name for ST-elevation myocardial infarction (MI), which is a more precise definition for a type of heart attack. It is caused by a prolonged period of blocked blood supply that affects a large area of the heart. A non-STEMI myocardial infarction may also occur.

Thrombosis is the formation of a blood clot inside a blood vessel, obstructing the flow of blood through the circulatory system. When a blood vessel is injured, the body uses platelets (thrombocytes) and fibrin to form a blood clot to prevent blood loss. Even when a blood vessel is not injured, blood clots may form in the body under certain conditions. A clot, or a piece of the clot, that breaks free and begins to travel around the body is known as an embolus. Thrombosis may occur in veins (venous thrombosis) or in arteries. Venous thrombosis leads to congestion of the affected part of the body, while arterial thrombosis (and rarely severe venous thrombosis) affects the blood supply and leads to damage of the tissue supplied by that artery (ischemia and necrosis).

NLRP3 (NOD-like receptor family, pyrin domain containing 3), also known as NALP3 or cryopyrin, is one of the sensors of the inflammasome, a macromolecular structure involved in interleukin-1β (IL-1β) and IL-18 processing. NLRP3 senses intracellular danger during intracellular infections (bacterial and viral proteins) or tissue injury (ischemia). NLRP3 activation leads to recruitment of ASC (apoptosis-associated speck-like protein containing carboxyterminal caspase recruitment domain) and caspase-1 leading to inflammasome formation and ultimately cell death. Growing evidence suggests a central role of the inflammasome in adverse cardiac remodeling after AMI leading to further dysfunction and HF. Cardiac remodeling and HF, however, are not complications limited to AMI and may occur also after non-ischemic injury.

Toldo et al (*Antioxid. Redox Signal,* 22: 1146-1161, 2015) report that following ischemic injury, the formation of the inflammasome, a macromolecular structure that amplifies the response by processing interleukin-1β and IL-18 and promotion of cell death, promotes adverse cardiac remodeling and heart failure.

Marchetti et al (*Cardiovasc Pharmacol,* 66: 1-8, 2015) report that pharmacological inhibition of the NLRP3 inflammasome limits cell death and LV systolic dysfunction after ischemic and nonischemic injury in mice.

There is a need for a method for treating cardiovascular diseases. The method should be effective and have no significant side effects.

BRIEF DESCRIPTION OF THE DRAWINGS

from J774A.1 cells following lipopolysaccharide (LPS)/adenosine triphosphate (ATP) stimulation in mouse J774A.1 cells.

DETAILED DESCRIPTION OF THE INVENTION

Figure 1:
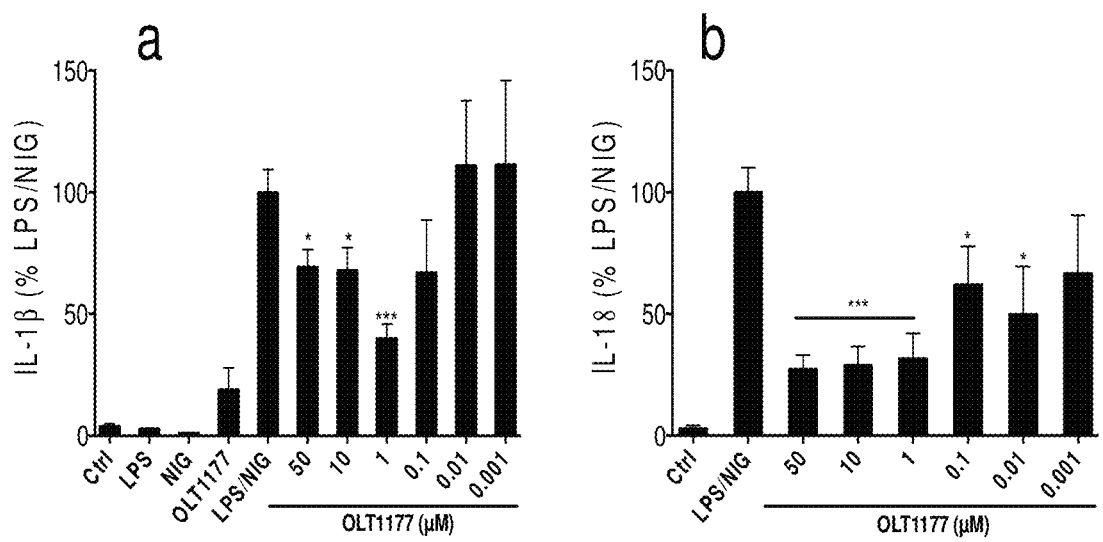
FIG. 1 shows the inhibition of IL-1β and IL-18 from human macrophages treated in vitro with dapansutrile.

Activation of the NLRP3 inflammasome amplifies the inflammatory response to tissue injury and mediates further damage. Dapansutrile is a selective NLRP3 inflammasome inhibitor; dapansutrile reduces inflammation by preventing activation of the NLRP3 inflammasome. Dapansutrile inhibits the production of IL-1β and IL-18 from human macrophages in vitro. Dapansutrile inhibits caspase-1 activation in human neutrophils and murine macrophages in vitro.

Through this mechanism of action, dapansutrile prevents the activation of caspase-1 and inhibits the formation of NLRP3 inflammasome in animals and human subjects. Dapansutrile prevents damaging effects of inflammation by blocking the assembly of the NLRP3 inflammasome and prevents the production of IL-1β and IL-18. Dapansutrile is effective in reducing infarct size and attenuating left ventricle systolic dysfunction after myocardial ischemia/reperfusion in subjects. Dapansutrile is effective in preserving cardiac function after ischemic and non-ischemic injury in subjects.

The present invention is directed to methods of treating cardiovascular disease such as acute myocardial infarction, atherosclerosis, heart failure, stroke, thrombosis, carditis (including acute myocarditis, acute pericarditis and complicated pericarditis), cardiac allograft rejection, cardiomyopathy, and peripheral vascular diseases.

Compound

The present invention uses a purified compound of dapansutrile (3-methanesulfonyl-propionitrile), or the pharmaceutically acceptable salts thereof:

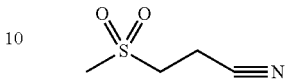

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4+$ (wherein X is $C_{1-4}$).

Pharmaceutical Compositions

The active compound dapansutrile, or its pharmaceutically acceptable salt or solvate in the pharmaceutical compositions in general is in an amount of about 0.1-5% for an injectable formulation, about 1-90% for a tablet formulation, 1-100% for a capsule formulation, about 0.01-20%, 0.05-20%, 0.1-20%, 0.2-15%, 0.5-10%, or 1-5% (w/w) for a topical formulation, and about 0.1-5% for a patch formulation.

"About" as used in this application, refers to ±10% of the recited value.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and ploxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of dapansutrile may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of dapansutrile may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethylether.

Topical formulations including dapansutrile can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethylether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent). In one embodiment, diethylene glycol monoethylether is included in the topical gel formulation.

Method of Use

By inhibiting assembly of the NLRP3 inflammasome, dapansutrile prevents the activation of caspase-1 and the subsequent maturation of pro-IL-1β and pro-IL-18 to proinflammatory cytokines IL-1β and IL-18, respectively.

Dapansutrile inhibits the processing and release of IL-1β, but not the synthesis of the IL-1β precursor and the other inflammasome components including NLRP3 and ASC. Dapansutrile also inhibits caspase-1 activation. Moreover, dapansutrile preserves the body's immune surveillance by not suppressing other inflammasomes such as NLRC4 and AIM2, constitutive cytokines and by protecting from cell death.

The present invention is directed to methods of treating cardiovascular diseases such as acute myocardial infarction, atherosclerosis, heart failure, stroke, thrombosis, carditis (including acute myocarditis, acute pericarditis and complicated pericarditis), cardiac allograft rejection, cardiomyopathy, and peripheral vascular diseases. The above cardiovascular diseases all have an inflammatory component either as a cause of the disease or as a result of an event. The method comprises the step of administering to a subject in need thereof an effective amount of dapansutrile. "An effective amount," as used herein, is the amount effective to treat a disease by ameliorating the pathological condition, and/or reducing, improving, and/or eliminating the symptoms of the disease.

In one embodiment, the present invention is effective in treating acute pericarditis, including refractory/relapsing acute pericarditis. In one embodiment, the present invention is effective in preventing recurrences of acute pericarditis. By administering dapansutrile to a subject (e.g., patient) suffering from acute pericarditis, the patient has reduced symptoms associated with acute pericarditis, such as chest pain, fatigue, fever, chest tightness, widespread ST-segment elevation, PR depressions not reported previously, pericardial effusion, recurrent pain, fever, pericardial friction rub, ECG changes, echocardiographic evidence of pericardial effusion, elevated white blood cell count, erythrocyte sedimentation rate, high-sensitivity C-reactive protein (hsCRP) levels, CRP levels, cardiac tamponade, constructive pericarditis, shortness of breath, and/or reduced or no recurrence of acute pericarditis.

In one embodiment, the present invention is effective in treating complicated pericarditis, including refractory/relapsing complicated pericarditis. In one embodiment, the present invention is effective in preventing recurrences of complicated pericarditis. By administering dapansutrile to a patient suffering from acute pericarditis, the patient has reduced symptoms associated with acute pericarditis, such as chest pain, fatigue, fever, chest tightness, widespread ST-segment elevation, PR depressions not reported previously, pericardial effusion, recurrent pain, fever, pericardial friction rub, ECG changes, echocardiographic evidence of pericardial effusion, elevated white blood cell count, erythrocyte sedimentation rate, hsCRP levels, cardiac tamponade, constructive pericarditis, shortness of breath, and/or reduced or no recurrence of acute pericarditis.

In one embodiment, the present invention is effective in treating myocarditis, including refractory/relapsing myocarditis. In one embodiment, the present invention is effective in preventing recurrences of myocarditis. By administering dapansutrile to a patient suffering from myocarditis, the patient improves one or more of the following symptoms associated with myocarditis: chest pain, dizziness, fatigue, malaise, abnormal heart rhythm, murmur, palpitations, fast breathing, shortness of breath, and swelling of one or more of the patient's extremities.

In one embodiment, the present invention is effective in treating cardiac allograft rejection, including refractory/relapsing cardiac allograft rejection. In one embodiment, the present invention is effective in preventing recurrences of cardiac allograft rejection. By administering dapansutrile to a patient suffering from cardiac allograft rejection, the patient has improved levels of hsCRP, IL-1β and/or IL-6, improved cardiopulmonary exercise testing (CPX) values, improved graft acceptance and/or graft survival, reduced inflammation, and a lack of subsequent hospitalization for an indication associated with cardiac allograft rejection.

In one embodiment, the present invention is effective in treating heart failure, including refractory/relapsing heart failure. In one embodiment, the present invention is effective in preventing recurrences of heart failure. By administering dapansutrile to a patient suffering from heart failure, the patient has improved pharmacodynamic endpoints and/or biomarker endpoints, such as levels of plasma hsCRP, IL-1β and IL-6, and/or B-type Natriuretic Peptide (BNP). The patient in general also has improved CPX scores, improved ECG recordings, and/or improved bioimpedance analysis, and/or has a reduced risk of being re-hospitalized for an indication associated with heart failure. In one embodiment, the present invention is effective in treatment of STEMI for the prevention of heart failure.

In one embodiment, the present invention is effective in treating AMI, including refractory/relapsing AMI. In one embodiment, the present invention is effective in preventing recurrences of AMI. By administering dapansutrile to a patient suffering from AMI, the patient has a reduction in left ventricular end-diastolic diameter, end-systolic diameter, area of damaged cardiac tissue, and/or infarct size.

Treatment with dapansutrile inhibits the NLRP3 inflammasome formation in models of ischemia/reperfusion AMI or non-reperfusion AMI and causes a significant reduction in infarct size measured at pathology or as serum cardiac troponin I level. Inhibition of the NLRP3 inflammasome preserves cardiac function and attenuates LV systolic dysfunction after ischemic; and nonischemic injury.

In one embodiment, the present invention is effective in treating atherosclerosis, including refractory/relapsing atherosclerosis. In one embodiment, the present invention is effective in preventing recurrences of atherosclerosis. By administering dapansutrile to a patient suffering from atherosclerosis, the patient has an improved mean vessel wall area ratio, improved plaque burden in one or more affected vessels, improved distensibility of one or more affected vessels, improved peak oxygen consumption scores, improved peak oxygen consumption (peak $VO_2$) change, improved ventilatory efficiency, improved left ventricular ejection fraction, improved diastolic function, reduced or lack of subsequent hospitalization for one or more indications associated with atherosclerosis, improved pulse wave velocity, improved plaque composition, reduced aortic strain, improved hsCRP levels, improved fasting plasma glucose, improved HbA1c levels, improved glucose post oral glucose tolerance test, improved beta cell function (HOMA-B), improved insulin resistance (HOMA-IR), and/or a reduced serum amyloid A (SAA) level.

In one embodiment, the present invention is effective in treating cardiomyopathy, including refractory/relapsing cardiomyopathy. In one embodiment, the present invention is effective in preventing recurrences of cardiomyopathy. By administering dapansutrile to a patient suffering from cardiomyopathy, the patient has reduced chest pain, reduced dizziness, reduced fatigue, increased appetite, improved heart rhythm, reduced heart rate, reduced incidence of heart murmur, reduced bloating, reduced abdominal fluid, reduced coughing, reduced instances of shortness of breath, reduced swelling of one or more of the patient's extremities, and/or reduced weight gain.

In one embodiment, the present invention is effective in treating stroke, including refractory/relapsing stroke. In one embodiment, the present invention is effective in preventing recurrences of stroke. By administering dapansutrile to a patient suffering from stroke, the patient has reduced lesion volume, reduced brain inflammatory levels, increased probability of recovery on the mRS score, and/or reduced cytotoxic edema.

In one embodiment, the present invention is effective in treating thrombosis, including refractory/relapsing thrombosis. In one embodiment, the present invention is effective in preventing recurrences of thrombosis. By administering dapansutrile to a patient suffering from thrombosis, the patient has improved flow-reduction (e.g., increased blood flow) in one or more vessels having one or more thrombi or having been exposed to one or more thrombi, increased cyclic flow variations preceding formation of one or more thrombi (such as an occlusive thrombi), a reduced number of clots, reduced formation of thrombi, and/or reduced histological evidence of thrombosis.

In one embodiment, the present invention is effective in treating peripheral vascular disease, including refractory/relapsing peripheral vascular disease. In one embodiment, the present invention is effective in preventing recurrences of peripheral vascular disease. By administering dapansutrile to a patient suffering from peripheral vascular disease, the patient has reduced vessel wall area ratio(s), reduced SAA levels and/or ratios, and/or reduced hsCRP levels and/or ratios.

The pharmaceutical composition of the present invention can be applied by systemic administration or local administration. Systemic administration includes, but is not limited to oral, parenteral (such as intravenous, intramuscular, subcutaneous or rectal), and inhaled administration. In systemic administration, the active compound first reaches plasma and then distributes into target tissues. Oral administration is a preferred route of administration for the present invention. Local administration includes topical administration.

Dosing of the composition can vary based on the extent of the injury and each patient's individual response. For systemic administration, plasma concentrations of the active compound delivered can vary; but are generally $1 \times 10^{-10}$-$1 \times 10^{-4}$ moles/liter, and preferably $1 \times 10^{-8}$-$1 \times 10^{-5}$ moles/liter.

In one embodiment, the pharmaceutical composition is administrated orally to a subject. The dosage for oral administration is generally 0.1-100, 0.1-20, or 1-50 mg/kg/day, depending on the subject's age and condition. For example, the dosage for oral administration is 0.1-10, 0.5-10, 1-10, 1-5, or 5-50 mg/kg/day for a human subject. In one embodiment, the active compound can be applied orally to a human subject at 1-100, 10-50, 20-1000, 20-500, 100-800, or 200-600 mg/dosage, 1-4 times a day, depends on the patient's age and condition.

In one embodiment, the pharmaceutical composition is administrated intravenously to a subject. The dosage for intravenous bolus injection or intravenous infusion is generally 0.03 to 5 or 0.03 to 1 mg/kg/day.

In one embodiment, the pharmaceutical composition is administrated subcutaneously to the subject. The dosage for subcutaneous administration is generally 0.3-20, 0.3-3, or 0.1-1 mg/kg/day.

In one embodiment, the composition is applied topically. The composition is topically applied at least 1 or 2 times a day, or 3 to 4 times per day, depending on the medical issue and the disease pathology. In general, the topical composition comprises about 0.01-20%, or 0.05-20%, or 0.1-20%, or 0.2-15%, 0.5-10, or 1-5% (w/w) of the active compound. Typically, 0.2-10 mL of the topical composition is applied to the individual per dose.

Those of skill in the art will recognize that a wide variety of delivery mechanisms are also suitable for the present invention.

The present invention is useful in treating a mammal subject, such as humans, horses, dogs and cats. The present invention is particularly useful in treating humans.

The following examples further illustrate the present invention. These examples are intended merely to be illustrative of the present invention and are not to be construed as being limiting.

EXAMPLES

Example 1. Suppression of IL-1β and 11-18 Release from Human Monocytes-Derived Macrophages Peripheral blood mononuclear cells (PBMCs) were isolated from blood of 6 healthy human donors and differenciates in macrophages using GM-CSF (5 ng/ml) for 5 days. They were stimulated with 1 µg/mL with lipopolysaccharide (LPS, priming phase) at time zero. At 30 minutes, they were incubated with different concentrations of dapansutrile (OLT1177™) from 0.001-100 µM. At 4 hours, 10 µM of nigericin (NIG, release phase) was added. At the end of an 5 hour incubation period, the supernatant was harvested and assayed for IL-1β or IL-18 using respective ELISA kits following manufacturer's protocols. The results are shown in FIG. 1 (A and B).

FIG. 1a shows data on the suppression of IL-1β release from human monocytes-derived macrophages, following stimulation with lipopolysaccharide (priming phase) and nigericin (release phase). Maximum suppression effect was observed at 1 µM of dapansutrile.

FIG. 1b shows data on the suppression of IL-18 release from human monocytes-derived macrophages, following stimulation with lipopolysaccharide and NIG. Maximum suppression effects were observed at 10-50 µM of dapansutrile.

The results show that dapansutrile suppresses the release of IL-1β (FIG. 1a) and IL-18 (FIG. 1b) from stimulated monocytes-derived macrophages. ***: P<0.001, *: P<0.05, compared to control.

Example 2. Mouse IL-1β Levels

Zymosan injected directly into the knee joint of mice elicits an inflammatory response and is used as a model of arthritis (Verschure et al, Ann. Rheum Dis. 53:455-460, 1994). Endpoints measured in this model include knee joint swelling score, cytokine levels in the synovial tissue and microscopic pathology of the knee.

Arthritis was induced in mice by intra-articular injection of zymosan (180 µg) into the knee joint (at time zero) of both knees in each mouse. Mice were treated by oral gavage with vehicle (saline, n=5) or dapansutrile (drug) in vehicle (600 mg/kg, n=4) at times −25 hr, −13 hr, and −1 hr. After zymosan injection at time zero, mice were further treated with vehicle or dapansutrile (600 mg/kg) at times +11 hr and +23 hr. Mice were terminated 24 hours after the zymosan injection.

Macroscopic joint swelling was assessed on all knees after the skin is removed using a scoring system ranging from 0 to 3, with 0 being no swelling and 3 being severe swelling. The results showed that dapansutrile-treated mice had a significant reduction in the joint swelling, when compared with vehicle-treated mice.

Figure 2:
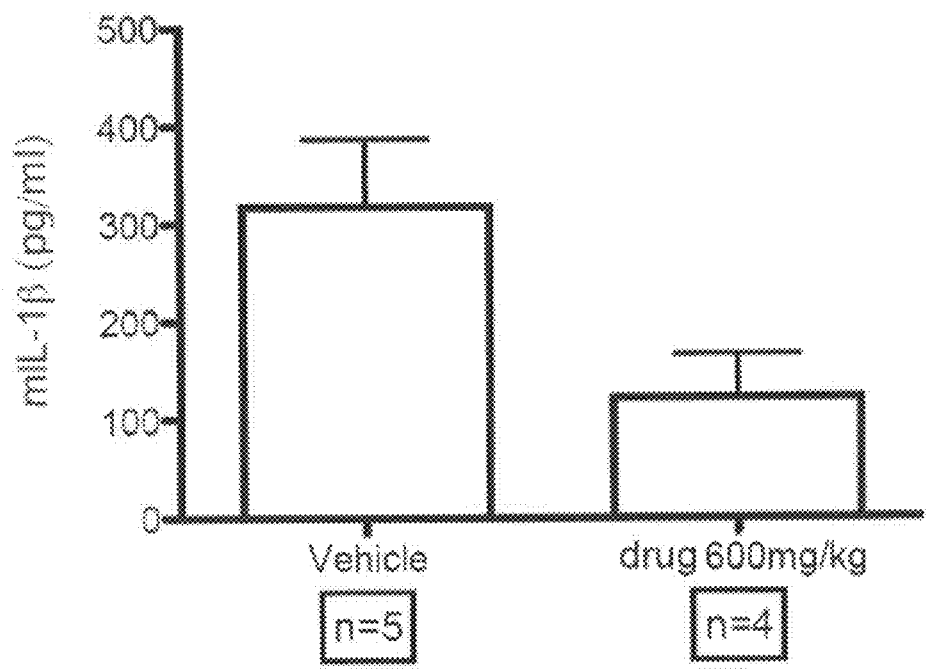
FIG. 2 shows that the level of IL-1β in synovial membrane was significantly reduced in mice treated with dapansutrile comparing with untreated mice.

In addition, synovial membrane was taken from one knee per mouse and the cells were lysed for measurement of mouse IL-1β, using an ELISA kit from R&D Systems, Inc., following manufacturer's protocols. The results are shown as mean±standard error of mean and statistical evaluation is performed (see FIG. 2). FIG. 2 shows that the level of IL-1β in synovial membrane was significantly reduced in mice treated with dapansutrile comparing with untreated mice.

Example 3. Inhibition of Caspase-1 Activation by Dapansutrile

J774A.1 murine macrophages cells were stimulated with 1 µg/ml lipopolysaccharide (LPS) for 4 hours and either nigericin (NIG, 10 µM) or ATP (5 mM) was added for 1 hour. OLT1177™ was added to the cells either 30 minutes following LPS stimulation or at the same time as ATP.

Figure 3A:
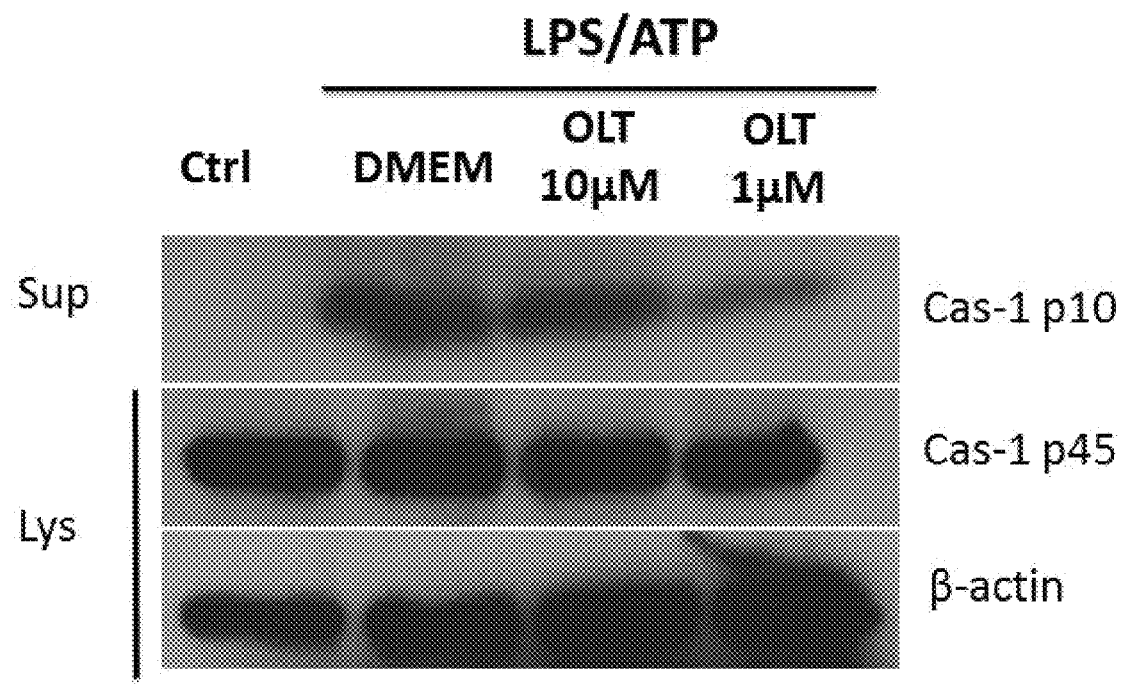
FIG. 3A shows the results of Western blots for caspase-1 (p45 and p10) of cell lysates (Lys) and supernatant (Sup)

FIG. 3A shows the results of Western blots for caspase-1 (p45 and p10) of cell lysates (Lys) and supernatant (Sup) from J774A.1 cells following LPS/ATP stimulation in mouse J774A.1 cells. A subunit of activated caspase-1 (p10) was reduced in J774A.1 cells in the presence of dapansutrile (OLT).

Figure 3B:
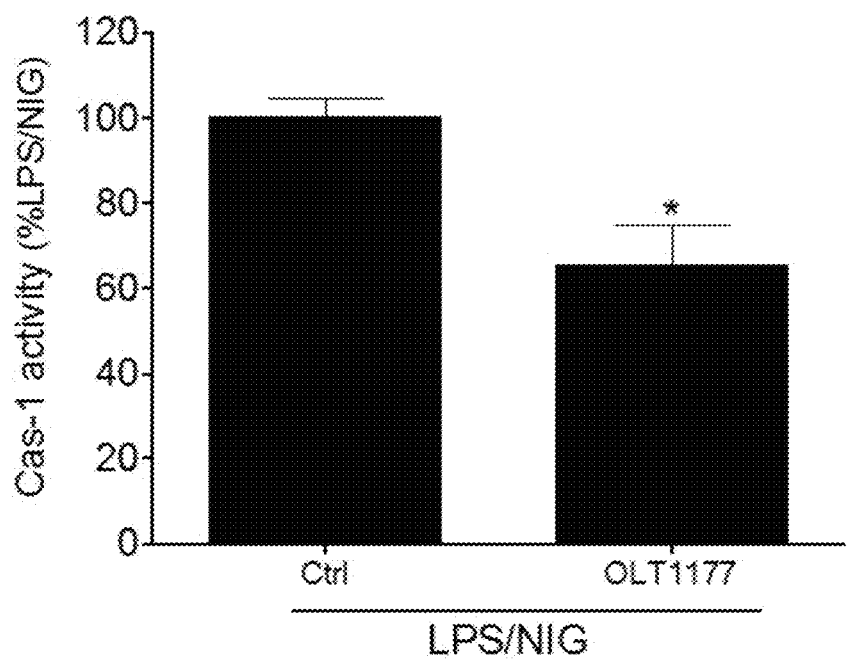
FIG. 3B shows the results of mean±SEM of caspase-1 activity in J774A.1 cell lysates following LPS and nigericin (NIG) stimulation in presence of 50 μM dapansutrile (or lab code, OLT1177™).

FIG. 3B shows the results of Mean±SEM of caspase-1 activity in J774A.1 cell lysates following LPS and NIG stimulation in presence of 50 µM dapansutrile (OLT1177™). Caspase-1 activity is expressed as percent change of the mean value of each assay (n=3) with LPS/NIG set at 100%. Caspase-1 activity was reduced by 35% (p<0.05) in an enzymatic assay of cell lysate from stimulated cells in the presence of dapansutrile, comparing with control.

The results show that dapansutrile (OLT1177™) inhibited caspase-1 activation in J774A.1 cell line.

Example 4. Inhibition of Inflammasome Assembly/Aggregation by Dapansutrile

Human monocyte-derived macrophages (HMDM) were cultured on glass slides for 5 days with GM-CSF, stimulated for 4 hours with 1 µg/ml LPS and then treated with 5 mM ATP for one hour. Dapansutrile (OLT1177™, 50 µM) was added to the cells either 30 minutes following LPS stimulation or at the same time as ATP.

After washing with PBS, the cells were fixed and permeabilized with 70-30 acetone-methanol as described by Gamboni et al, *Physiol Rep.*, 2(7), 2014. Briefly, cells were placed in a humidified slide chamber blocked for 1 hour in 10% normal donkey serum (Jackson Immunologicals, Westgrove, Pa.). After removal of the donkey serum, the primary antibodies to human NLRP3 (Cryo-2, AdipoGen San Diego, Calif.), human caspase-1 (sc-515, Santa Cruz Biotechnology) or isomolar, species-specific anti-IgG (R&D Systems) were added and kept overnight at 4° C. The slides were then washed three times with PBS and cells were incubated for 1 hour at room temperature with donkey anti-mouse-Alexa555 (Life Technologies) or donkey anti-rabbit-Alexa488 (Life Technologies) fluorochrome-conjugated secondary antibodies. Nuclei were stained with DAPI (Life Technologies). FRET images were acquired using a Marianas Imaging Station using a Zeiss 639 Plan-Apochromat objective (1.4 N/A), a Sutter Xenon light source and a Cooke Sensi-Cam as described by Gamboni et al. The corrected FRET was calculated as FRET=Transfer-Fd/D donor-Fa/Aa acceptor as reported by Berney et al, *Biophys J.*, 84: 3992-4010, 2003.

The formation of the NLRP3 inflammasome was examined using immunofluorescence and Fluorescent Resonance Energy Transfer (FRET) analysis in HMDM following stimulation with LPS and ATP. In unstimulated cells, caspase-1 (green) and NLRP3 (red) were diffuse in the cell. Following LPS/ATP, caspase-1 and NLRP3 localized to the submembrane area, and FRET analysis shows that caspase-1 associates with NLRP3 following stimulation. FRET positivity requires the distance between two molecules, in this case NLRP3 and caspase-1, to be less than 30 nm. In the presence of 50 µM OLT1177™, the association was reduced (P<0.01).

Figure 4:
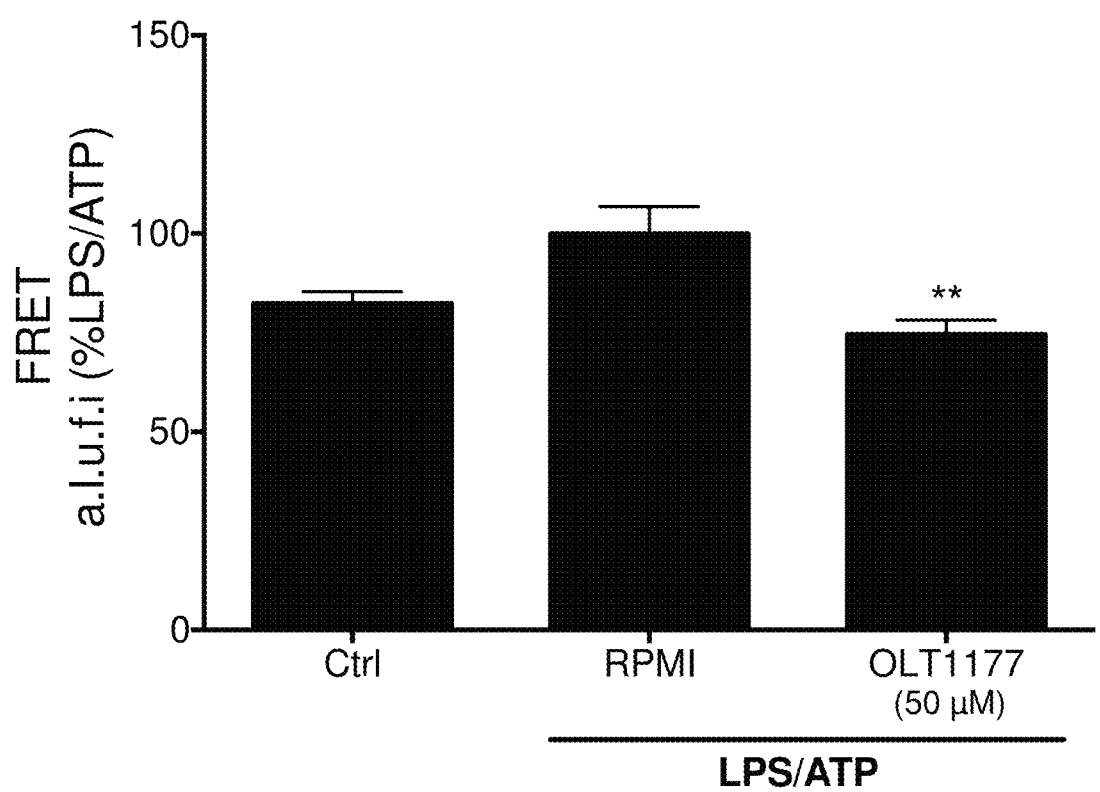
FIG. 4 shows mean±SEM percent change of FRET intensity of human monocyte-derived macrophages (HMDM) from 4 healthy donors following LPS/ATP stimulation in presence of OLT1177™ (50 μM).

FIG. 4 shows mean±SEM percent change of FRET intensity of HMDM from 4 healthy donors following LPS/ATP stimulation in presence of OLT1177™ (50 µM). **: P<0.01. The results of FRET microscopy demonstrate inhibition of inflammasome assembly/aggregation in dapansutrile treated cells. The FRET data are consistent with dapansutrile's suppression of caspase-1 and inhibition of IL-1β processing.

Example 5. Cytokine Levels after In Vivo Lipopolysaccharide Challenge

C57BL/6J mice male mice, 22-26 grams (Jackson Laboratories, Bar Harbor, Me.) were treated with 200 mg/kg dapansutrile (OLT1177™) in 200 μl of saline or the matching volume of vehicle (saline) intraperitoneally (IP) every 12 hours for 5 doses. One hour after the last dose or saline, the animals were injected IP with 200 μl of lipopolysaccharide (LPS, E. coli, 055:B5, Sigma-Aldrich) at 5 mg/kg and sacrificed after 2 h. Cytokines were measured in hearts homogenates. Tissue homogenates were lysed using RIPA buffer (Sigma-Aldrich) containing a mixture of protease inhibitors (Roche, Indianapolis, Ind.), centrifuged at 13,000 g for 20 minutes at 4° C., and the supernatants were assayed for cytokine levels of IL-1β, IL-6 and IL-1α. The cytokine concentrations were corrected for total protein content.

Figure 5:
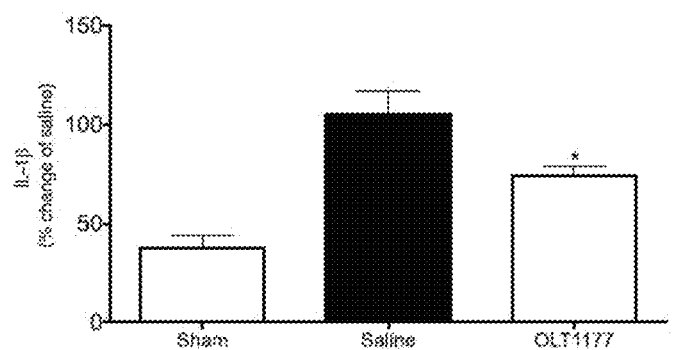
FIG. 5 shows that cytokine levels of IL-1β, IL-6 and IL-1α in hearts of mice after dapansutrile treatment and in vivo LPS challenge.
Figure 5:
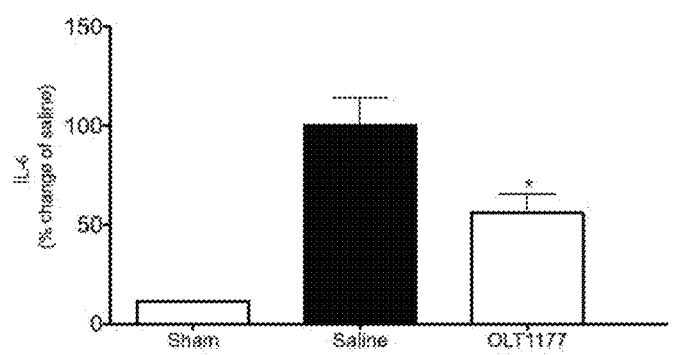
Figure 5:
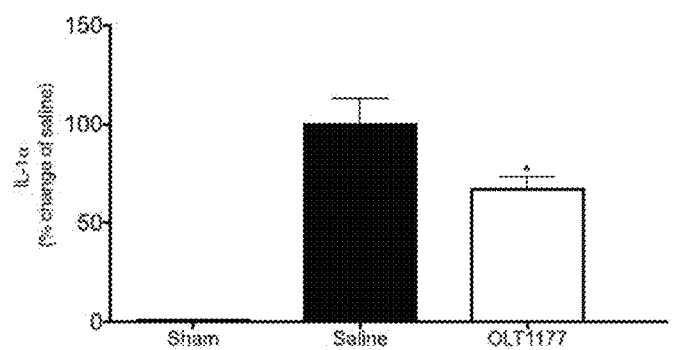

FIG. 5 shows that cytokine levels of IL-1β, IL-6 and IL-1α in hearts of mice after LPS challenge were reduced after drug treatment comparing with saline vehicle treatment with P value <0.05. The results indicate that dapansutrile reduces inflammation in the heart during inflammation. The dose of LPS that was used in the study covers ischemic inflammation, vascular inflammation and cell-mediated inflammation.

Example 6. Protocols for Treating Acute Myocardial Infarction (Ischemia/Reperfusion) with Dapansutrile in Animals Mice were orotracheally intubated under anesthesia (pentobarbital, 50-70 mg/kg), placed in the right lateral decubitus position, and then subjected to left thoracotomy, pericardiectomy, and ligation of the left anterior descending (LAD) coronary artery. The ligated coronary artery is released after 30 minutes before closure of the thorax. Sham operations are performed wherein animals undergo the same surgical procedure without coronary artery ligation. Mice are treated intraperitoneally with dapansutrile (60 mg/kg) or vehicle (saline) at reperfusion and then killed after 24 hours of reperfusion for the measurement of cardiac troponin I level and assessment of infarct size.

For troponin I level measurement, the blood of each mouse is drawn from the inferior vena cava and collected in Vacutainer tubes (BD Vacutainer, Franklin Lakes, N.J.) for serum isolation. Mouse troponin I levels are determined by enzyme-linked immunosorbent assay (Life Diagnostic Inc, West Chester, Pa.). Infarct size assessment is performed according to Toldo et al, *J Mol Cell Cardiol* 51: 244-51, 2011.

Example 7. Protocol for Treating Acute Myocardial Infarction (Permanent Ligation) with Dapansutrile in Animals This model reflects a more severe AMI than the model of Example 6. Mice are orotracheally intubated under anesthesia (pentobarbital, 50-70 mg/kg), placed in the right lateral decubitus position, and then subjected to left thoracotomy, pericardiectomy, and permanent ligation of the left anterior descending (LAD) coronary artery. Sham operations are performed wherein animals undergo the same surgical procedure without coronary artery ligation. Mice are treated intraperitoneally with dapansutrile (60 mg/kg) or vehicle (saline) immediately after ligation and then killed on day 7 for pathology after undergoing echocardiography to measure LV dimensions and function. Infarct size is performed according to Abbate et al, *Circulation,* 117: 2670-83, 2008.

Example 8. Infarct Sparing Effect of Dapansutrile in Animals

Figure 6:
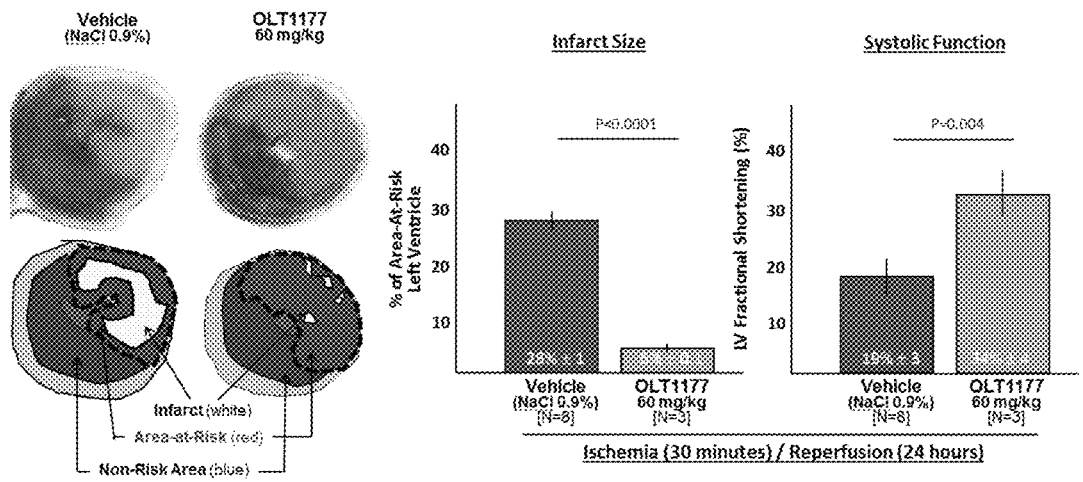
FIG. 6 shows that treating acute myocardial infarction in mice with OLT1177™ reduced infarct size and preserved left ventricular systolic function.

An acute myocardial infarction in adult CD1 male mice was induced by performing a transient surgical ligation of the left coronary artery for 30 minutes followed by reperfusion for 24 hours: 3 mice received OLT1177™ (60 mg/kg) given intraperitoneally immediately after reperfusion and 8 mice received an equal volume of vehicle (NaCl 0.9%). After 24 hours, left ventricular fractional shortening, a surrogate for cardiac systolic function, was measured, using transthoracic echocardiography. After the echocardiogram, the mice were prepared for infarct size measurement using the Triphenyl-Tetrazolium-Chloride (TTC) and Evans Blue technique and then sacrificed: the area of the heart considered not ischemia (non-risk area) appeared blue, the area of the heart that was at risk but viable appeared red, the infarct myocardium appeared pale-white. The left panel of FIG. 6 depicts the TTC/Evans Blue staining of one mouse treated with vehicle and one with OLT1177™: it is apparent that the area of infarct is much larger in the vehicle. The central panel quantifies infarct size expressed as percentage of the area-at-risk, showing a significantly smaller infarct size in mice treated with OLT1177™ compared to the vehicle-treated mice. The right panel shows preservation of left ventricular systolic function in mice treated with OLT1177™, as compared with vehicle-treated mice.

Example 9. Treatment of Acute Myocardial Infarction with Dapansutrile in Animals Objectives:
To determine the efficacy of, (1) a single dose of OLT1177™ (6, 60 and 600 mg/kg) administered at the time of reperfusion (Part A) and, (2) a single dose of 60 mg/kg OLT1177™ administered 60, 120 or 180 minutes after reperfusion in an experimental mouse AMI model.

Methodology:
Male CD-1 mice underwent transient surgical ligation of the left coronary artery for 30 minutes followed by reperfusion for 24 hours. A single dose of OLT1177™ (6, 60, or 600 mg/kg) or matching vehicle was administered intraperitoneally (IP) at time of reperfusion (N=5-9/group, Study Part A) or OLT1177™ (60 mg/kg) after a 60-, 120- or 180-minute delay (N=4-7/group, Study Part B). Echocardiography was performed to measure left ventricular (LV) fractional shortening (FS). Infarct size was measured at pathology by triphenyl-tetrazolium-chloride (TTC) and phthalo blue staining and expressed as a percentage of the myocardium at risk.

For the 60-mg/kg dose, OLT1177™ (13 mg/vial) was diluted in 0.65 ml of 0.9% of normal saline solution to reach a concentration of 20 mg/ml. For the 6 mg/kg dose, the 20 mg/ml dose was diluted 10 times (0.1 ml OLT1177™ 20 mg/kg+0.9 ml 0.9% normal saline) to reach a final concentration of 2 mg/ml. For the 600 mg/kg dose, each vial of OLT1177™ (13 mg/vial) was diluted with 0.1 ml of saline, to reach a final concentration of 130 mg/ml. The content of multiple vials was combined. Each respective tube was subjected to a vortex and heating at 37° C. until complete dissolution of the drug substance.

Male mice were dosed with OLT1177™ by the intraperitoneal route at dose levels of 6, 60, or 600 mg/kg (each approximately 33 g mouse received 100 µl of the dosing solution; 150 µl for the higher dose) after the reperfusion was confirmed (Study Part A). In Part B, 60 mg/kg OLT1177™ was injected (100 µl of the dosing solution per mouse) with a delay of 60, 120 or 180 minutes from the time of reperfusion.

Adult out-bred male CD1 mice (8-10 weeks of age) were supplied by Envigo (Indianapolis, Ind.). A single operator performed all surgeries. Experimental AMI was induced by transient coronary artery ligation for 30 minutes to induce ischemia of the anterior wall and the apex (visible as pallor) followed by reperfusion, and leading to an infarct involving approximately 15% of the left ventricle. Mice were deeply sedated with sodium pentobarbital (70 mg/kg), intubated using a 23 G catheter and placed in the right lateral decubitus. The mice were shaved and the skin was cleaned with povidone solution and isopropyl alcohol. The mice were then connected to a ventilator and a left thoracotomy was performed followed by pericardiectomy and ligation of the proximal left coronary artery. A 1-mm diameter polyethylene tube was inserted inside the ligature knot, secured and left in place to obstruct the coronary flow for 30 minutes. At the end of the ischemic time, the tube was removed and the coronary flow re-establishment was observed. At this time, OLT1177™ at a dose of 6, 60 or 600 mg/kg, or the normal saline (0.9% NaCl) used as vehicle (0.1 ml of total volume) was injected into the peritoneal cavity after the reperfusion was confirmed (Part A). After closure of the thoracic access, the mice were left to recover for 24 hours. Pain management was achieved using buprenorphine (Buprenorphine SR™ Lab, 0.5 mg/kg) injected subcutaneously. For Study Part B, groups of mice were injected with 60 mg/kg of OLT1177™ after 60, 120 or 180 minutes from the moment of reperfusion.

Only the mice that showed evidence of ischemia at visual inspection during surgery and involving the whole apex were randomly assigned to treatment groups by a surgery assistant not involved in the adjudication of the endpoints of interest.

Before sacrifice (24 hours after reperfusion), the mice underwent transthoracic echocardiography under mild anesthesia with sodium pentobarbital (50 mg/kg). Echocardiography was performed with the Vevo770 Imaging System (VisualSonics Inc, Toronto, Ontario, Canada) and a 30 MHz probe. The heart was visualized in B-mode from the parasternal short axis and apical views. The left ventricular (LV) end-diastolic diameter (LVEDD) and LV end-systolic diameters (LVESD) at M-Mode were measured. From these assessments, LV fractional shortening (FS) was calculated:

$$LVFS = \frac{(LVEDD - LVESD)}{LVEDD} \times 100\%$$

Ejection fraction (EF) was calculated using the Teichholz Formula by the Vevo software. The investigators performing and reading the echocardiogram were blinded to the treatment allocation.

Infarct size was measured 24 hours after surgery. Mice were exsanguinated and the hearts were quickly perfused with phosphate buffered saline (PBS) 1× pH 7.4 containing heparin (40 U/ml). After the blood was washed out, 10% triphenyltetrazolium chloride in PBS 1× was perfused into the coronary arteries, the ligated coronary artery was closed again and the coronaries where antegradely infused with 1% Phthalo blue dye (Quantum Ink, Louisville, Ky., USA) in 5 mM adenosine in PBS 1× until most of the heart turned blue. The PBS and TTC was perfused through the LV apex using a fine needle; the blue dye was injected from the aorta using an intravenous catheter.

After, the hearts were explanted, frozen and cut into 6-8 transverse slices of equal thickness (i.e., about 1 mm) from apex to base. The hearts were thawed to 37° C. degrees for 5 minutes and 10% formaline was added to the heart sections for 30 minutes to increase color contrast. The infarcted tissue (appearing white) and the viable tissue (bright red) were measured by computer morphometry using Image Pro Plus 6.0 software (Media Cybernetics, Silver Spring, Md.). Infarct size was reported as the percent of the area of the left ventricle.

Outcomes:

The parameters measured in this study include (N=4-9 animals/group):

Left ventricular (LV) end-diastolic diameter
Left ventricular (LV) end-systolic diameter
Infarct size Results:

OLT1177™ (6, 60 and 600 mg/kg) administered as a single intraperitoneal injection at the time of reperfusion provided a significant reduction in infarct size (p<0.001) associated with a preservation of left ventricular systolic function (Tables 1-5).

The low dose of 6 mg/kg OLT1177™ demonstrated a 36% decrease in infarct size compared to the vehicle control. Mean infarct size for the mid- and high-dose groups (60 and 600 mg/kg) was more than 60% decreased compared to the vehicle control. The reduction in infarct size was also associated with a preservation of left ventricular systolic function. In fact, both LV fractional shortening and ejection fraction calculated at 24 hours after reperfusion were significantly higher for all doses of OLT1177™ relative to the vehicle control group (p<0.05).

Figure 7:
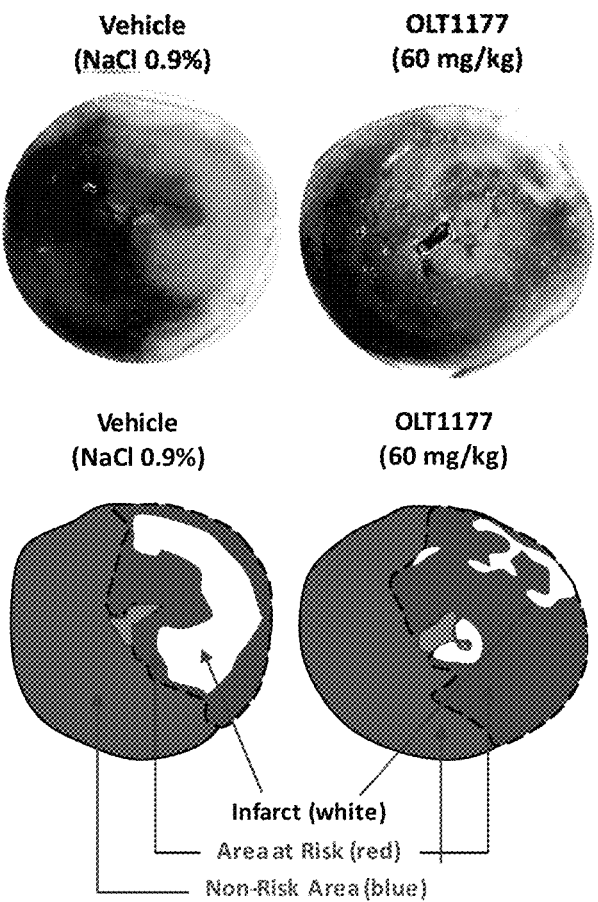
FIG. 7 shows representative images of triphenyl tetrazolium chloride- and phthalo blue-stained ventricular heart sections for infarct size measurement in mice treated with vehicle and 60 mg/kg OLT1177™.
Figure 8:
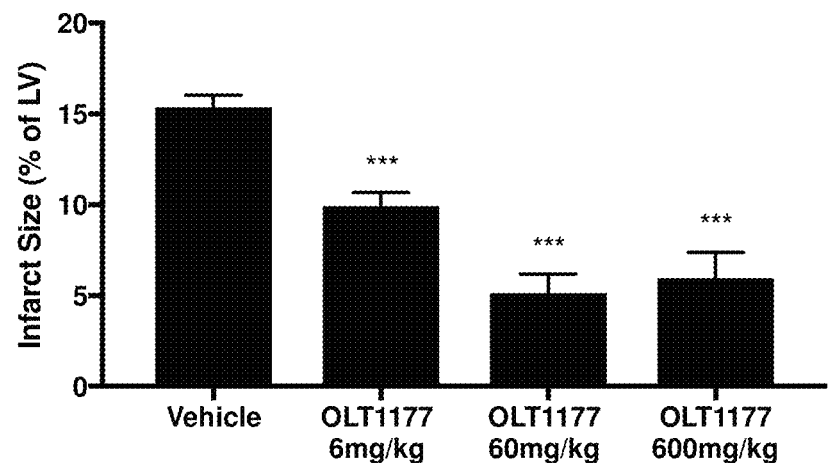
FIG. 8 shows the mean (±SEM) percent of left ventricular infarct size 24 hours following ischemia/reperfusion for mice administered 6, 60 or 600 mg/kg OLT1177™ or vehicle at the time of reperfusion in study part A.
Figure 9A:
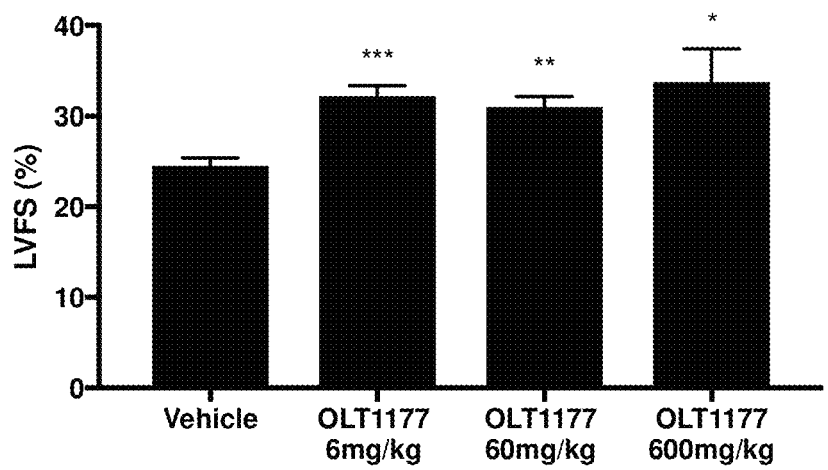
FIGS. 9A and 9B show the mean (±SEM) left ventricular fractional shortening (FIG. 9A) and left ventricular ejection fraction (FIG. 9B) 24 hours following ischemia/reperfusion for mice administered 6, 60 or 600 mg/kg OLT1177™ or vehicle at the time of reperfusion in study part A.
Figure 9B:
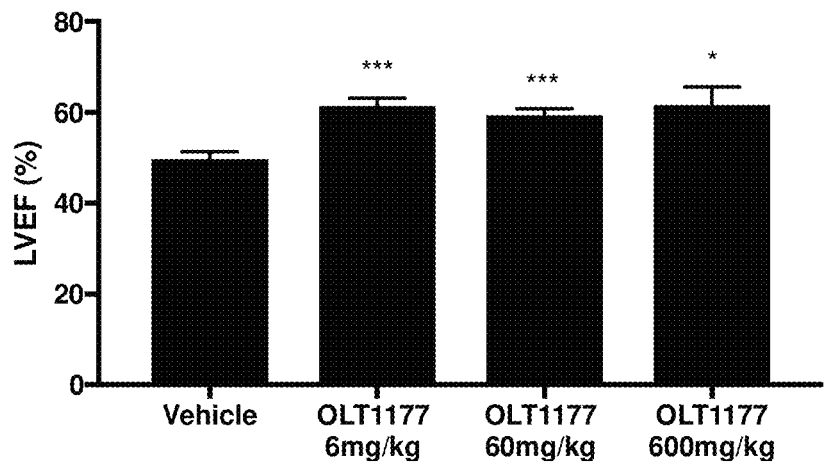

OLT1177™ administered as an intraperitoneal injection at the time of reperfusion in study Part A led to a significant reduction in infarct size measured with TTC when compared with vehicle alone (FIG. 7). Mean infarct size in the vehicle-treated group was 15.4% compared to 9.9%, 5.1% and 6.0% after a single dose of 6, 60 or 600 mg/kg of OLT1177™, respectively (FIG. 8; p<0.001). There was no significant difference in infarct size between the mid- and high dose groups (p>0.05). The reduction in infarct size was also associated with a preservation of left ventricular systolic function. In fact, both LV fractional shortening and ejection fraction calculated at 24 hours after reperfusion were significantly higher for all doses of OLT1177™ relative to the vehicle control group (FIGS. 9A and 9B; p<0.05).

Figure 10:
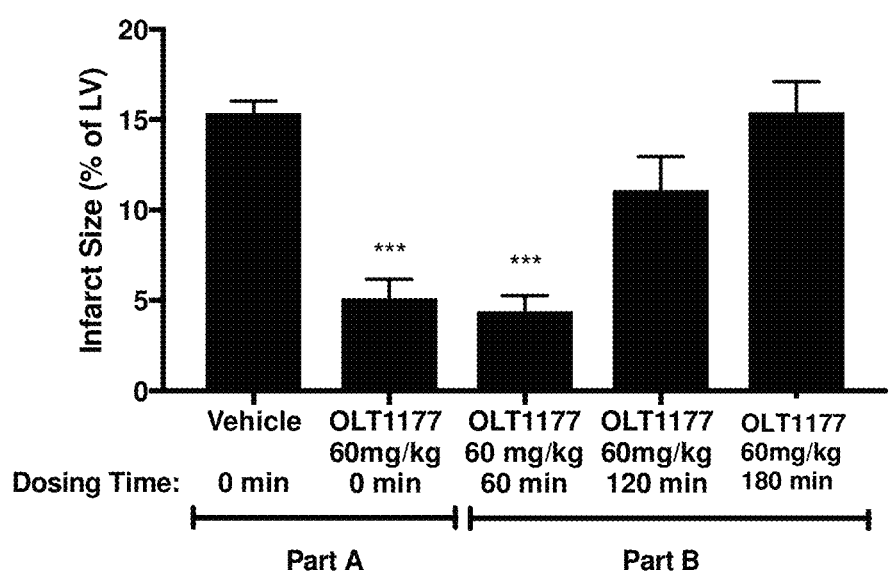
FIG. 10 shows the mean (±SEM) percent of left ventricular infarct size 24 hours following ischemia/reperfusion for mice administered 60 mg/kg OLT1177™ either 60, 120 or 180 minutes after reperfusion in study part B compared to at the time of reperfusion in study part A.
Figure 11A:
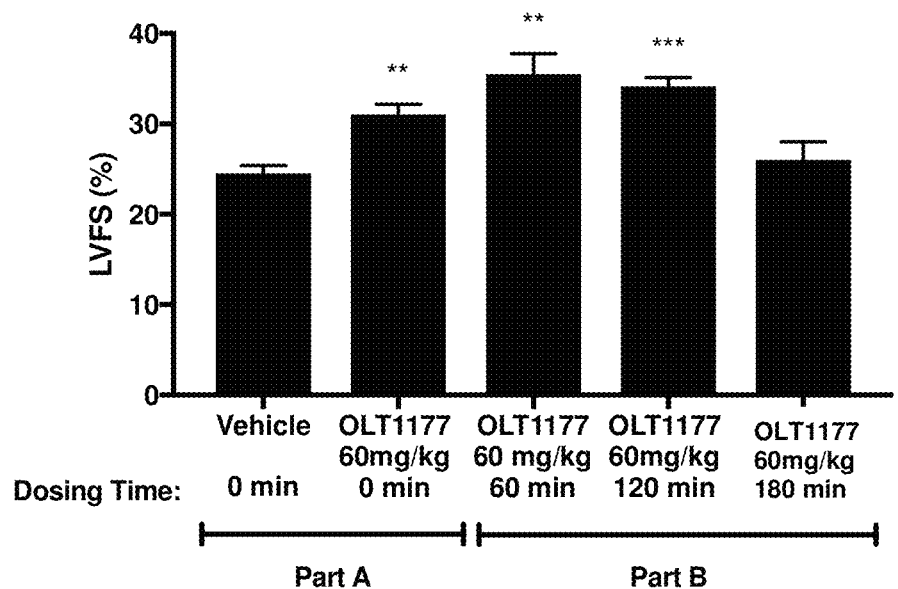
FIGS. 11A and 11B show the mean (±SEM) left ventricular fractional shortening (FIG. 11A) and left ventricular ejection fraction (FIG. 11B) 24 hours following ischemia/reperfusion for mice administered 60 mg/kg OLT1177™ 60, 120 or 180 minutes after reperfusion in study part B compared to at the time of reperfusion in study part A.
Figure 11B:
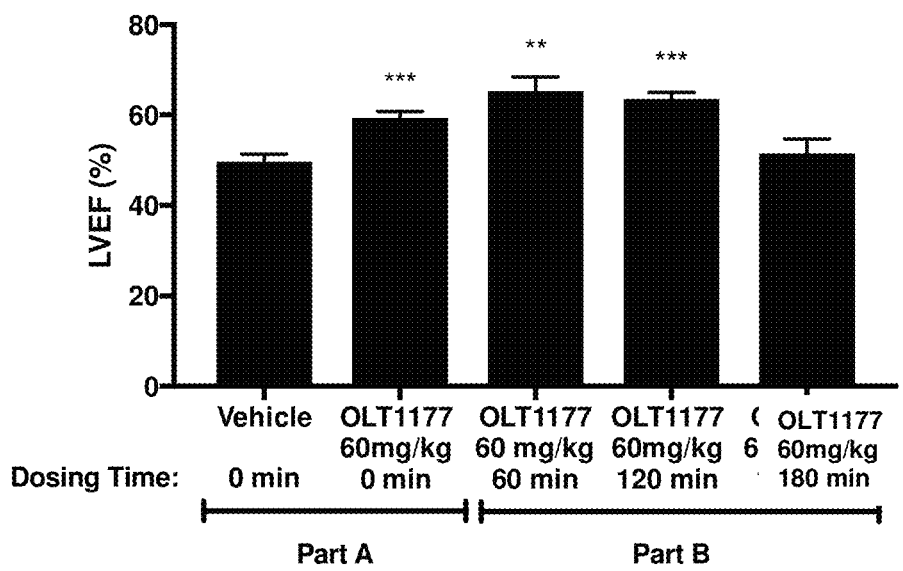

As the minimal effective dose from study Part A, 60 mg/kg OLT1177™ was selected to be administered either 60, 120 or 180 minutes after reperfusion in Part B. As such, OLT1177™ given after a 60 minutes delay after reperfusion was equally effective at reducing infarct size and preserving LV function as the treatment given with no delay in Part A. Infarct size was not significantly altered when OLT1177™ 60 mg/kg was administered 120 or 180 minutes after reperfusion (FIG. 10). After a treatment delay of 60 or 120 minutes, LV fractional shortening and ejection fraction were significantly improved in comparison to vehicle-treated mice (FIGS. 11A and 11B; p<0.01). After a treatment delay of 180 minutes however, OLT1177™ failed to prevent the drop in fractional shortening or to reduce the infarct size.

TABLE 1

Study Design and Dose Groups

| Study Part | Group | Treatment | Dose Regimen | Route of Administration | Time of Dosing[1] | Number of Males Infarct Size Measurement | Echo Data |
|---|---|---|---|---|---|---|---|
| A | 1 | 0.9% Saline Injection | Single dose | IP | 0 min | 7 | 6 |
|   | 2 | 6 mg/kg OLT1177 ™ | Single dose | IP | 0 min | 9[2] | 5 |
|   | 3 | 60 mg/kg OLT1177 ™ | Single dose | IP | 0 min | 5[3] | 9 |
|   | 4 | 600 mg/kg OLT1177 ™ | Single dose | IP | 0 min | 5 | 5 |
| B | 5 | 60 mg/kg OLT1177 ™ | Single dose | IP | 60 min | 5 | 7[4] |
|   | 6 |   |   |   | 120 min | 7 | 7 |
|   | 7 |   |   |   | 180 min | 4 | 4 |

BID: Twice daily;

IP: Intraperitoneally

[1] Relative to time of reperfusion

[2] One sample was not properly stained; therefore, N = 8 for analyses

[3] No infarct was observed in one animal; therefore, N = 4 for analyses

[4] No reperfusion in one animal; therefore, N = 6 for analyses

TABLE 2

Summary Data by Group - Infarct Size after 30 Minutes of Ischemia and Test Article Dosing at the Time of Reperfusion (Part A)

| Group 1 0.9% Saline | | Group 2 6 mg/kg OLT1177 ™ | | Group 3 60 mg/kg OLT1177 ™ | | Group 4 600 mg/kg OLT1177 ™ | |
|---|---|---|---|---|---|---|---|
| Mean | 15.4 | Mean | 9.9 | Mean | 5.1 | Mean | 6.0 |
| SE | 0.65 | SE | 0.90 | SE | 1.05 | SE | 1.41 |
| N | 7 | N | 8 | N | 4 | N | 5 |
| Change (%)[1] | NA | Change (%)[1] | −36% | Change (%)[1] | −67% | Change (%)[1] | −61% |
| p-value[1,2] | NA | p-value[1,2] | 0.0005 | p-value[1,2] | 0.000002 | p-value[1,2] | 0.00005 |

LV: Left ventricle;

$LV_{ent}$: Entire LV;

$LV_{cav}$: LV cavity;

NA: Not applicable;

ND: Not determined;

SE: Standard error

[1] Relative to saline group

[2] Unpaired 2-tailed t-test

[3] Not properly stained

[4] No infarct observed

TABLE 3

Summary Data by Group - Infarct Size after 30 Minutes of Ischemia with a Delay in Test Article Dosing by 60, 120 or 180 Minutes (Part B)

| | Group 5<br>60 mg/kg<br>OLT1177 ™<br>Administered<br>at 60 Minutes | | Group 6<br>60 mg/kg<br>OLT1177 ™<br>Administered<br>at 120 Minutes | | Group 7<br>60 mg/kg<br>OLT1177 ™<br>Administered<br>at 180 Minutes | |
|---|---|---|---|---|---|---|
| Mean | 4.4 | Mean | 11.1 | Mean | 15.4 |
| SE | 0.86 | SE | 1.86 | SE | 1.69 |
| N | 5 | N | 7 | N | 4 |
| p-value[1,2] | 0.000001 | p-value[1,2] | 0.0517 | p-value[1,2] | 0.9804 |
| p-value[2,3] | 0.6400 | p-value[2,3] | 0.0126 | p-value[2,3] | 0.0003 |

LV: Left ventricle;
$LV_{ent}$: Entire LV;
$LV_{cav}$: LV cavity;
NA: Not applicable;
ND: Not determined;
SE: Standard error
[1] Relative to saline group in Part A (Group 1)
[2] Unpaired 2-tailed t-test
[3] Relative to 60 mg/kg administered at time of reperfusion (Group 3)

TABLE 4

Summary Echocardiogram Data by Group - Parameters after 30 Minutes of Ischemia and Test Article Dosing at the Time of Reperfusion (Part A)

| | Group 1 0.9%<br>Saline (N = 6) | | Group 2 6 mg/kg<br>OLT1177 ™ (N = 5) | | | Group 3 60 mg/kg<br>OLT1177 ™ (N = 9) | | | Group 4 600 mg/kg<br>OLT1177 ™ (N = 5) | | |
|---|---|---|---|---|---|---|---|---|---|---|---|
| | Mean | SEM | Mean | SEM | p-value[1] | Mean | SEM | p-value[1] | Mean | SEM | p-value[1] |
| LVEDD (mm) | 4.00 | 0.099 | 3.71 | 0.108 | 0.0794 | 4.25 | 0.163 | 0.2677 | 3.76 | 0.210 | 0.2903 |
| LVESD (mm) | 3.01 | 0.104 | 2.52 | 0.111 | 0.0101 | 2.93 | 0.100 | 0.5799 | 2.54 | 0.219 | 0.0666 |
| AWDT (mm) | 0.74 | 0.014 | 0.79 | 0.041 | 0.2060 | 0.82 | 0.028 | 0.0411 | 0.77 | 0.032 | 0.4459 |
| PWDT (mm) | 0.85 | 0.028 | 0.86 | 0.032 | 0.7902 | 0.86 | 0.025 | 0.7223 | 0.83 | 0.018 | 0.5786 |
| AWST (mm) | 0.99 | 0.070 | 1.10 | 0.058 | 0.2617 | 1.25 | 0.032 | 0.0021 | 1.06 | 0.040 | 0.4102 |
| PWST (mm) | 1.27 | 0.068 | 1.12 | 0.068 | 0.1620 | 1.24 | 0.029 | 0.7207 | 1.14 | 0.057 | 0.1870 |
| LVFS (%) | 24.5 | 0.885 | 32.2 | 1.158 | 0.0004 | 31.0 | 1.143 | 0.0012 | 33.0 | 2.828 | 0.0125 |
| LVEF (%) | 49.7 | 1.726 | 61.4 | 1.691 | 0.0010 | 59.3 | 1.424 | 0.0008 | 61.6 | 3.982 | 0.0167 |

AWDT: Anterior wall diastolic thickness;
AWST: Anterior wall systolic thickness;
LVEDD: Left ventricular end-diastolic diameter;
LVEF: Left ventriclular ejection fraction;
LVESD: Left ventricular end-systolic diameter;
LVFS: Left ventricular fractional shortening;
PWDT: Posterior wall diastolic thickness;
PWST: Posterior wall systolic thickness;
SEM: Standard error of mean
[1] Unpaired 2-tailed t-test, relative to saline group (Group 1)

TABLE 5

Summary Echocardiogram Data by Group - Parameters after 30 Minutes of Ischemia with a Delay in OLT1177 ™ Dosing by 60, 120 or 180 Minutes (Part B)

| | Group 1 0.9%<br>Saline<br>(N = 6, Part A) | | Group 5 60 mg/kg<br>OLT1177 ™<br>Administered at 60<br>Minutes (N = 6) | | | Group 6 60 mg/kg<br>OLT1177 ™<br>Administered at 120<br>Minutes (N = 7) | | | Group 7 60 mg/kg<br>OLT1177 ™<br>Administered at 120<br>Minutes (N = 4) | | |
|---|---|---|---|---|---|---|---|---|---|---|---|
| | Mean | SEM | Mean | SEM | p-value[1] | Mean | SEM | p-value[1] | Mean | SEM | p-value[1] |
| LVEDD (mm) | 4.00 | 0.099 | 4.00 | 0.140 | 0.9773 | 4.07 | 0.064 | 0.5869 | 3.88 | 0.134 | 0.4682 |
| LVESD (mm) | 3.01 | 0.104 | 2.59 | 0.163 | 0.0513 | 2.68 | 0.064 | 0.01729 | 2.87 | 0.119 | 0.39642 |
| AWDT (mm) | 0.74 | 0.014 | 0.85 | 0.038 | 0.0227 | 0.83 | 0.025 | 0.0121 | 0.95 | 0.048 | 0.00097 |
| PWDT (mm) | 0.85 | 0.028 | 0.89 | 0.030 | 0.3904 | 0.87 | 0.039 | 0.6230 | 0.94 | 0.030 | 0.0681 |

TABLE 5-continued

Summary Echocardiogram Data by Group - Parameters after 30 Minutes of Ischemia with a Delay in OLT1177 ™ Dosing by 60, 120 or 180 Minutes (Part B)

|  | Group 1 0.9% Saline (N = 6, Part A) | | Group 5 60 mg/kg OLT1177 ™ Administered at 60 Minutes (N = 6) | | | Group 6 60 mg/kg OLT1177 ™ Administered at 120 Minutes (N = 7) | | | Group 7 60 mg/kg OLT1177 ™ Administered at 120 Minutes (N = 4) | | |
|---|---|---|---|---|---|---|---|---|---|---|---|
|  | Mean | SEM | Mean | SEM | p-value[1] | Mean | SEM | p-value[1] | Mean | SEM | p-value[1] |
| AWST (mm) | 0.99 | 0.070 | 1.18 | 0.029 | 0.0286 | 1.20 | 0.044 | 0.0217 | 1.22 | 0.035 | 0.0366 |
| PWST (mm) | 1.27 | 0.068 | 1.33 | 0.063 | 0.5547 | 1.26 | 0.075 | 0.3762 | 1.31 | 0.033 | 0.6911 |
| LVFS (%) | 24.5 | 0.885 | 35.5 | 2.247 | 0.0011 | 34.1 | 1.010 | 0.00002 | 26.0 | 2.000 | 0.4593 |
| LVEF (%) | 49.7 | 1.726 | 65.3 | 3.106 | 0.0013 | 63.6 | 1.445 | 0.00006 | 51.5 | 3.175 | 0.5948 |

AWDT: Anterior wall diastolic thickness;
AWST: Anterior wall systolic thickness;
LVEDD: Left ventricular end-diastolic diameter;
LVEF: Left ventriclular ejection fraction;
LVESD: Left ventricular end-systolic diameter;
LVFS: Left ventricular fractional shortening;
PWDT: Posterior wall diastolic thickness;
PWST: Posterior wall systolic thickness;
SEM: Standard error of mean
[1]Unpaired 2-tailed t-test relative to saline group (Group 1, Part A)

Example 10. Treatment of Acute Myocardial Infarction with Dapansutrile (Prophetic Example)

Objectives:

To investigate the efficacy of dapansutrile, formulated as a capsule for oral administration to patients, in treating patients, and/or improving patient outcomes following AMI.

Formulation:

The formulation for use in this example is a capsule containing a blend of 100 mg of dapansutrile and Avicel® PH-101. Each placebo capsule contains only Avicel® PH-101. Both the dapansutrile capsules and the placebo capsules are formulated for oral administration.

Methodology:

A randomized, double-blind, placebo-controlled, event driven clinical activity study of daily orally administered dapansutrile in treatment of AMI among stable post-MI patients with elevated high sensitivity C-reaction protein (hsCRP or CRP).

Patients with prior AMI (>30 days) and elevated CRP (CRP>2 mg/11) who also have reduced left ventricular ejection fraction (LVEF<50%) and are symptomatic for heart failure (New York Heart Association symptoms 'NYHA' class are offered to take part in this study. Patients undergo a cardiopulmonary exercise test (CPX) at baseline prior to initiation of treatment, and then repeat at 3 and 12 months, and a transthoracic echocardiogram at baseline and at 12 months.

Inclusion Criteria:
Written informed consent
Male, or Female of non-child-bearing potential
Age≥18 years
Spontaneous myocardial infarction (MI) at least 30 days before randomization
hsCRP≥2 mg/L
LVEF<50%
NYHA class II-III
Exclusion Criteria:
Pregnant or nursing (lactating) women
Women of child-bearing potential
Any of the following concomitant diseases
　Planned coronary revascularization PCI or CABG
　Major non-cardiac surgical or endoscopic procedure within past 6 months
　Multi-vessel CABG surgery within the past 3 years
　Symptomatic patients with Class IV HF
　Uncontrolled hypertension
　Uncontrolled diabetes
Inability to complete a treadmill exercise test
Conditions preventing interpretation of the cardiopulmonary test (arrhythmias, ischemia, hypertension, pulmonary disease)
Criteria for Evaluation (can Include One or More of the Following, but is not Limited to any of the Following):
Clinical Activity:

The study performs serial Cardiopulmonary Exercise Tests (CPX) to prospectively measure changes in aerobic exercise capacity in patients with prior MI, elevated CRP levels, and symptomatic heart failure with reduced systolic function, randomly assigned to dapansutrile or placebo.

The subjects enrolled in this study undergo repeated CPX and echocardiograms over the first 12 months of the trial.

Study Endpoints:
The primary clinical activity endpoint is:
Peak oxygen consumption ($VO_2$) [Time Frame: 3 months]
　Difference in the interval change from baseline in peak $VO_2$ at 3 months following a single dose of dapansutrile 100 mg oral or a double dose of dapansutrile 100 mg oral when compared with the interval change in placebo (placebo-corrected interval change).
The secondary clinical activity endpoints are:
Peak $VO_2$ change [Time Frame: 12 months]
　Difference in the interval changes from baseline and 12 months in peak $VO_2$ comparing dapansutrile (both doses) with placebo.
Ventilatory efficiency (VE/$VCO_2$ slope) change [Time Frame: 12 months]
　Difference in the interval changes from baseline and 3 months in the VE/$VCO_2$ slope comparing dapansutrile (both doses) with placebo.
Oxygen Utilization Efficiency Slope (OUES) [Time Frame: 12 months]
　Difference in the interval changes from baseline and 12 months in OUES comparing dapansutrile (both doses) with placebo.

LVEF change [Time Frame: 12 months]
  Difference in the interval changes from baseline and 12 months in LVEF comparing dapansutrile (both doses) with placebo.
Diastolic function change [Time Frame: 12 months]
  Difference in the interval changes from baseline and 12 months in E/E' (diastolic function) comparing dapansutrile (both doses) with placebo.

Example 11. Treatment of Atherosclerosis with Dapansutrile (Prophetic Example)

Objectives:
To investigate the efficacy of dapansutrile, formulated as a capsule for oral administration to patients, in treating atherosclerosis. More specifically, to evaluate the effect of daily administration of oral dapansutrile capsules compared with placebo on a patient's plaque burden measured by integrated vascular MRI.

Formulation:
The formulation used in this example is a capsule containing a blend of 100 mg of dapansutrile and Avicel® PH-101. Each placebo capsule contains only Avicel® PH-101. Both the dapansutrile capsules and the placebo capsules are formulated for oral administration.

Methodology:
A randomized, double-blind, placebo-controlled, event driven clinical activity study of daily orally administered dapansutrile in treatment of atherosclerosis among stable post-MI patients with elevated hsCRP.

Inclusion Criteria:
Written informed consent
Male, or Female of non-child-bearing potential
Age ≥18 years.
Spontaneous MI at least 30 days before randomization.
hsCRP ≥2 mg/L
Acquisition of evaluable baseline MRI images of bilateral carotid arteries by an imaging laboratory Exclusion Criteria:
Pregnant or nursing (lactating) women
Women of child-bearing potential
Any of the following concomitant diseases
  Planned coronary revascularization (PCI or CABG)
  Major non-cardiac surgical or endoscopic procedure within past 6 months
  Multi-vessel CABG surgery within the past 3 years
  Symptomatic patients with Class IV heart failure (HF).
  Uncontrolled hypertension
  Uncontrolled diabetes
  Patients with prior history of carotid angioplasty, stenting, or carotid atherectomy
  Patients with contraindications to MRI examination (brain aneurysm clip, implanted neural stimulator, implanted cardiac pacemaker, pacemaker wires or defibrillator, prosthetic heart valves, cochlear implant, ocular foreign body or other implanted body, tattoos, implanted insulin pump, metal shrapnel or bullet)
  Patients prone to claustrophobia or known anxiety disorders Criteria for Evaluation (can Include One or More of the Following, but is not Limited to any of the Following):
Clinical Activity:
The study determines the efficacy of daily orally administered dapansutrile in the prevention and/or treatment of atherosclerosis among stable post-myocardial infarction patients with elevated hsCRP.

Study Endpoints:
The primary clinical activity endpoints can include, but are not limited to:
Mean vessel wall area ratio of 12 months to baseline [Time Frame: Baseline, 12 months post-dose]
  Peripheral artery wall area (superficial femoral artery) measured using Magnetic Resonance Imaging (MRI) cross-section slices. Mean vessel wall area ($mm^2$) is derived by converting total plaque volume (TPV) (mL) of the vessel to $mm^3$ by multiplying by 1000, dividing by the number of slices used for the volume calculation, and dividing by the thickness of a slice (3 mm). Least squares mean for ratio of 12 months to baseline is measured from repeated measures mixed effect model with visit, treatment, the treatment-by-visit interaction, baseline and the visit-by-baseline interaction as fixed effects.
Change from baseline in carotid plaque burden in the bifurcation region of the index carotid artery [Time Frame: 36 months]
Number of participants with adverse events, serious adverse events and death [Time Frame: 12 months]
  Participants are monitored for adverse events, serious adverse events and death throughout the study, such as nonfatal MI, nonfatal stroke, or cardiovascular death.
Change from baseline in aortic elasticity [Time Frame: baseline, 3 months, 12 months]
  Two axial, ECG-gated, steady state free precession (SSFP) 'cine' images are acquired during breath-hold to determine aortic distensibility. The first image is obtained at the level of the right pulmonary artery through the ascending and proximal descending aorta and the second through the distal aorta below the diaphragm. Imaging of the aorta also allows evaluation of the plaque burden and additional vascular function measures.
Change from baseline in plaque burden (aortic vessel wall area and carotid vessel wall area) [Time Frame: baseline, 3 months, 12 months]
  For assessment of atherosclerotic plaque burden of the aorta, vessel wall images of the aorta is acquired with an echocardiogram (ECG) gated double-inversion recovery (black blood) fast spin echo sequence applied breath-holding. Using an oblique sagittal image of the aorta as a pilot, serial axial images are acquired to cover a section of the descending thoracic aorta. The midpoint of the right pulmonary artery in cross section is used as the anatomical reference for the first slice in baseline and follow-up scans. For assessment of the atherosclerotic plaque burden in the carotids, vessel wall images are acquired with an axial ECG gated PD (proton density) weighted black blood sequence. The carotid bifurcation is used as the anatomical reference for all three imaging time points (baseline, 12 weeks, 48 weeks) with axial slice planes acquired below the bifurcation region. The mean values reported here for the carotid are reported for the proximal common carotid region.

The secondary clinical activity endpoints can include, but are not limited to:
Hospitalization for unstable angina that led to urgent revascularization.
Incidence of new-onset type 2 diabetes among patients with prediabetes at randomization in a time-to-event analysis Change from baseline of the total vessel wall area at Month 3 of the index carotid artery. [Time Frame: 36 months]

Mean total vessel wall area across the left and right carotid artery at Month 3 and Month 24. [Time Frame: 36 months]

Change from baseline in corresponding total vessel wall area in the left and right carotid arteries. [Time Frame: 36 months]

The existence of a baseline total vessel wall area by treatment interaction as well as the consistency of the treatment effect across subgroups. [Time Frame: 36 months]

Change from baseline in pulse wave velocity and pulse wave velocity error [Time Frame: baseline, 3 months, 12 months]
   Utilizing the SphygmoCor Device, ECG leads are placed at the carotid and femoral arteries provided the measure of the pulse wave at that particular arterial location. The distance between the two vascular beds is divided by the pulse wave time shift provided a measure of the pulse wave velocity.

Change from baseline in plaque composition [Time Frame: baseline, 3 months, 12 months]
   During the carotid MRI acquisition, in addition to the proton density (PD) weighted ECG gated double inversion fast spin echo sequences T1 and T2 weighted sequences are acquired. In combination with the PD weighted images, the multi-contrast images are analyzed to determine regions of interest with contrast patterns consistent with the presence of necrotic lipid core, calcification and fibrous tissue in participants who have complex carotid plaque present in the bifurcation region.

Change from baseline in aortic strain [Time Frame: baseline, 3 months, 12 months]
   Arterial strain are computed directly from the cine steady-state free precession (SSFP) images and the change in lumen diameters over the cardiac cycle. The value is independent of pulse pressure and is unitless ratio derived from the maximum to minimum lumen diameters diastole and systole, respectively.

Change from baseline in hsCRP [Time Frame: baseline, 3 months, 12 months]
   Blood samples are collected to analyze hsCRP.

Change from baseline in fasting plasma glucose [Time Frame: baseline, 3 months, 12 months]
   Blood samples are collected to analyze fasting plasma glucose.

Change from baseline in Hemoglobin A1c (HbA1c) [Time Frame: baseline, 3 months, 12 months]
   Blood samples are collected to analyze HbA1c.

Change from baseline in 2 hour glucose post oral glucose tolerance test (OGTT) [Time Frame: baseline, 3 months, 12 months]
   Blood samples are collected to analyze the 2 hour glucose post OGTT.

Change from baseline in beta cell function (HOMA-B) [Time Frame: baseline, 3 months, 12 months]
   Blood samples are collected to analyze beta cell function. Beta cell function is calculated by the Homeostasis Model Assessments (of beta cell function (HOMA-B) as follows: HOMA-B: The product of 20 and basal insulin (µU/mL) levels divided by the value of basal glucose (mmol/L) concentrations minus 3.5 [i.e., HOMA-B=20*basal insulin/(basal glucose-3.5)].

Change from baseline insulin resistance (HOMA-IR) [Time Frame: baseline, 3 months, 12 months]
   Blood samples are collected to analyze insulin resistance. Insulin resistance is calculated by the Homeostasis Model Assessments of insulin resistance (HOMA-IR)) as follows: HOMA-IR: The product of basal glucose (mmol/L) and insulin (µU/mL) levels divided by 22.5 [i.e., HOMA-IR=basal glucose*basal insulin/22.5].

Serum Amyloid A (SAA) level ratio of 12 months to baseline [Time Frame: Baseline, 12 months post-dose]
   Least squares mean for ratio of 12 months to baseline is measured from repeated measures mixed effect model with visit, treatment, treatment-by-visit interaction, baseline and the visit-by-baseline interaction as fixed effects.

hsCRP ratio of 12 months to baseline [Time Frame: Baseline, 12 months post-dose]
   Least squares mean for ratio of 12 months to baseline is measured from repeated measures mixed effect model with visit, treatment, treatment-by-visit interaction, baseline and the visit-by-baseline interaction as fixed effects.

Example 12. Inhibition of Thrombus Formation in Anesthetized Rats by Dapansutrile To evaluate the effect of dapansutrile on thrombus formation in vivo, the following experimental protocol is performed.

Rats (CD-1; male; approximately 350 grams; Charles River, Raleigh, N.C.), are anesthetized with sodium pentobarbital (70 mg/kg i.p.). The abdomens are shaved and a 22 gauge intravenous catheter is inserted into a lateral tail vein. A midline incision is made and the intestines are wrapped in saline-soaked gauze and positioned so the abdominal aorta is accessible. The inferior vena cava and abdominal aorta are carefully isolated and a section (approximately 1 cm) of the abdominal aorta (distal to the renal arteries proximal to the bifurcation) is dissected. All branches from the aorta in this section are ligated with 4-0 silk suture. A 2.5 mm diameter flow probe connected to a Transonic flow meter is placed on the artery and a baseline (pre-stenosis) flow is recorded. Two clips are placed around the artery decreasing the vessel diameter by approximately 80%. A second baseline flow measurement is taken (post-stenosis) and the hyperemic response is tested. Animals are then treated with either Rho kinase inhibitor compound or saline intravenously via tail vein catheter. Thrombosis is induced five minutes after treatment by repeated external compressions of the vessel with hemostatic forceps. Two minutes post-injury, the vessel compressions are repeated and a 10 minute period of flow monitoring is started Animals are monitored continuously for a minimum of the first ten minutes post-injury. After twenty minutes (post-injury), a flow measurement is repeated and the animals are euthanized. The section of the aorta that includes the injured section is harvested and placed in 10% formalin for histological evaluation. Treatment with compound of dapansutrile results in a decrease in the vessel injury-induced flow reduction and histological evidence of thrombosis.

Example 13. Inhibition of Thrombus Formation in Anesthetized Dogs by Dapansutrile To evaluate the effect of compound of Formula I or II on dynamic thrombus formation in vivo, the following experimental protocol, similar to the method of J. L. Romson et al. (*Thromb. Res.* 17:841-853, 1980), is performed.

Surgical Preparation and Instrumentation.

Briefly, purpose-bred dogs are anesthetized, intubated and ventilated with room air. The heart is exposed by a left thoracotomy in the fifth intercostal space and suspended in a pericardial cradle. A 2-3 cm segment of the left circumflex coronary artery (LCCA) is isolated by blunt dissection. The artery is instrumented from proximal to distal with a flow probe, a stimulation electrode, and a Goldblatt clamp. The flow probe monitors the mean and phasic LCCA blood flow velocities. The stimulation electrode and its placement in the LCCA and the methodology to induce an occlusive coronary thrombus have been described previously (J. K. Mickelson et al., *Circulation* 81:617-627, 1990; R. J. Shebuski et al., *Circulation* 82:169-177, 1990; J. F. Tschopp et al., *Coron. Artery Dis.* 4:809-817, 1993).

Experimental Protocol:

Dogs are randomized to one of four treatment protocols in which the control group receives saline intravenously and the three drug-treated groups are administered Rho kinase inhibitor compound intravenously. Upon stabilization from the surgical interventions, dogs receive either saline or compound at different concentrations. After approximately 30 minutes, an anodal current is applied to the LCCA for 180 min. The number and frequency of cyclic flow variations (CFV) that precede formation of an occlusive thrombus are recorded. These cyclic phenomena are caused by platelet thrombi that form in the narrowed lumen as a result of platelet aggregation (J. D. Folts et al., *Circulation* 54:365-370, 1976; Bush et al., *Circulation* 69:1161-1170, 1984). Zero flow in the LCCA for a minimum of 30 minutes indicates a lack of antithrombotic efficacy (L. G. Frederick et al., *Circulation* 93:129-134, 1996). Treatment with compound of dapansutrile significantly increases the number and frequency of cyclic flow variations that precede the formation of an occlusive thrombus.

Example 14. Treatment of Thrombosis with Dapansutrile (Prophetic Example)

Objectives:

To investigate the efficacy of dapansutrile, formulated as a capsule for oral administration to patients, in treating and/or improving outcomes of patients who are experiencing or who have had thrombosis.

Formulation:

The formulation used in this example is a capsule containing a blend of 100 mg of dapansutrile and Avicel® PH-101. Each placebo capsule contains only Avicel® PH-101. Both the dapansutrile capsules and the placebo capsules are formulated for oral administration.

Methodology:

A randomized, double-blind, placebo controlled, parallel treatment clinical activity study.

Patients with unilateral proximal DVT and patients with SVT of the lower-extremity are included in this study. As control, volunteers without DVT or SVT, and without history of thromboembolism, are recruited.

Inclusion Criteria (can include one or more of the following, but is not limited to the following):
>18 years of age
acute, idiopathic or provoked, unilateral proximal DVT (involving the popliteal vein or further proximal veins)
SVT (more than 5 cm in length on compression ultrasonography) of the lower-extremity
Age and sex matched controls are recruited from volunteers after exclusion of DVT or SVT, and without history of thrombosis and pulmonary embolism Exclusion Criteria (can include one or more of the following, but is not limited to the following):
History of previous DVT or SVT of the lower-extremity
History of pulmonary embolism
Bilateral DVT or SVT
DVT associated with intravenous drug abuse, surgery of the lower-extremity in the previous 10 days, or sclerotherapy in the previous 30 days
Follow-up is not considered feasible
Heart failure (HYHA III or IV)
Acute coronary syndrome (<7d)
Severe pulmonal-arterial hypertension (pulmonal arterial pressure >90 mmHg)
Pregnancy Criteria for Evaluation (can Include One or More of the Following, but is not Limited to the Following):
Study Endpoints:
The primary clinical activity endpoint is:
improved blood flow through one or more of the patient's blood vessels
The secondary clinical activity endpoints are:
reduced histological evidence of thrombosis
a reduced number of blood clots
reduced formation of one or more thrombi Example 15. Treatment of Complicated Pericarditis with Dapansutrile (Prophetic Example Objectives:

To investigate the efficacy of dapansutrile, formulated as a capsule for oral administration to patients, in treating patients, and/or improving patient outcomes, in patients having complicated pericarditis.

Formulation:

The formulation for use in this example is a capsule containing a blend of 100 mg of dapansutrile and Avicel® PH-101. Each placebo capsule contains only Avicel® PH-101. Both the dapansutrile capsules and the placebo capsules are formulated for oral administration.

Methodology:

A randomized, double-blind, placebo-controlled, event driven clinical activity study of daily orally administered dapansutrile in treatment of patients having complicated pericarditis.

Patients having complicated pericarditis are screened for inclusion in the study. A diagnosis of complicated pericarditis is reached using one or more of the following techniques, cardiac magnetic resonance (CMR), chest x-ray, echocardiography, computerized axial tomography (CAT) scan, viral serology, and other specific testing according to the initial clinical presentation. Pericardiocentesis is performed when a bacterial or neoplastic etiology is suspected, if cardiac tamponade is suspected, or if severe pericardial effusion without response to medical therapy. In addition, a patient's pericardial thickness (e.g., using $T_1$ or $T_2$ weighted fast spin echo images), pericardial edema (e.g., $T_2$ short-tau inversion-recovery fast-spin echo images), pericardial inflammation (e.g., late gadolinium enhancement), and ventricular interdependence (e.g., cine imaging with short-axis images at the basal level with patients instructed to breathe deeply) can also be measured.

Study Endpoints:

The primary clinical activity endpoints are:

reduction in any two or more of the following symptoms:
- fever
- anterior chest pain
- friction rub
- normalized (or significantly reduced) hsCRP levels Example 16. Treatment of Acute Pericarditis in Mice with Dapansutrile (Prophetic Example Overview of Zymosan Mouse Model of Pericarditis:

Zymosan, a product of the yeast wall, known to specifically activate the NLRP3 inflammasome, is injected directly into the pericardial space of each mouse's heart. Pericardial inflammation is measured by echocardiography (pericardial thickening and effusion) and at pathology (pericardial thickening, expression of the active inflammasome), and then tested treatment with anti-inflammatory therapies such as colchicine.

Objectives:

To investigate the efficacy of dapansutrile in the mouse model of acute pericarditis caused by zymosan intrapericardial injection.

Methodology:

Adult mice (8-12 weeks of age) supplied by Harlan Laboratories (Harlan Sprague Dawley Inc.) are anesthetized and an initial transthoracic echocardiogram, as described below, is performed. The mice undergo a left thoracotomy and with direct visualization, a 30 Gauge needle is used to inject 1 mg of zymosan dissolved in 50 µl of sterile NaCl 0.9% into the pericardial space. The zymosan solution is distributed into the pericardium by carefully lifting the pericardial sac with forceps until a generally complete distribution occurs Sham procedures are performed by injecting an equal volume of sterile NaCl 0.9%.

Dapansutrile is administered either intraperitoneally or by oral gavage (final volume 100 µl) and an equivalent volume of matching vehicle is used as a control.

To test the effects of dapansutrile in the acute pericarditis model, the following outputs are used:

1. Acute dose-response of dapansutrile (6, 10, 60 and 600 mg/kg) given at the same time of zymosan, to determine efficacy;
2. Delayed Treatment with dapansutrile (using lowest dose with greatest efficacy) given on day 3 after zymosan injection;
3. Chronic preventative strategy tested with chronic administration of dapansutrile given through oral gavage (or chow or water) for 1-2 weeks prior to zymosan.

The Vevo770 imaging system (VisualSonics, Toronto, Canada) is used under light anesthesia. The left ventricle in the parasternal short axis view at the mid-ventricular level in the bi-dimensional mode (B-mode) is visualized. The image is optimized for the anterior wall, and the image is zoomed to visualize the anterior pericardial structures. After optimization of the image, a mono-dimensional mode (M-mode) is acquired for optimal spatial-temporal resolution and allowing for measurements of the pericardial fluid, defined as echo-free space between the 2 layers of the pericardium. Echocardiography is performed prior to surgery, and again at 3, 7, and 14 days, prior to sacrifice. Pilot studies demonstrate a peak in sterile inflammation between 3 and 7 days, and resolution by day 14. A person blinded to the group allocation measures maximal pericardial effusion in distance in both the M- and B-modes.

The heart is explanted after 7 or 14 days and is processed for pathology. Formalin fixed paraffin-embedded transverse sections of the hearts are stained with hematoxylin and eosin. A person blinded to group allocation measures the pericardial thickness with computer morphometry using Image Pro Plus 6.0 software (Media Cybernetics, Silver Spring, Md.).

The formation of the NLRP3 inflammasome in cells is a single speck visible at light microscopy after staining for ASC (e.g., apoptosis-associated speck-like protein containing a caspase-recruiting domain). Double immunofluorescence is used for ASC in combination with anti-α-cardiac actin to differentiate the pericardial from the myocardial structures.

Example 17. Treatment of Acute Pericarditis with Dapansutrile (Prophetic Example)

Objectives:

To investigate the efficacy of dapansutrile, formulated as a capsule for oral administration to patients, in treating patients, and/or improving patient outcomes, in patients having acute pericarditis.

Formulation:

The formulation for use in this example is a capsule containing a blend of 100 mg of dapansutrile and Avicel® PH-101. Each placebo capsule contains only Avicel® PH-101. Both the dapansutrile capsules and the placebo capsules are formulated for oral administration.

Methodology:

A randomized, double-blind, placebo-controlled, event driven clinical activity study of daily orally administered dapansutrile in treatment of acute pericarditis patients.

All consecutive cases of acute pericarditis within 24 hours from symptom onset are screened for inclusion in the study. A final diagnosis of idiopathic or viral acute pericarditis is reached by chest x-ray, echocardiography, viral serology, and other specific testing according to the initial clinical presentation. Pericardiocentesis is performed when a bacterial or neoplastic etiology is suspected, if cardiac tamponade is suspected, or if severe pericardial effusion without response to medical therapy after 1 week of therapy is observed.

Diagnostic criteria for acute pericarditis include pericarditic chest pain, pericardial friction rubs, widespread ST-segment elevation, and/or PR depressions not reported previously, and new or worsening pericardial effusion. A clinical diagnosis of acute pericarditis is made when at least two of these criteria were present. Criteria for the diagnosis of recurrence include recurrent pain and 1 or more of the following signs: fever, pericardial friction rub, ECG changes, echocardiographic evidence of pericardial effusion, and an elevation in the white blood cell count, erythrocyte sedimentation rate, or CRP.

Criteria for Evaluation (can Include One or More of the Following, but is not Limited to any of the Following):

Clinical Activity:

The study performs serial Cardiopulmonary Exercise Tests (CPX) to prospectively measure changes in aerobic exercise capacity in patients with prior MI, elevated CRP levels, and symptomatic heart failure with reduced systolic function, randomly assigned to dapansutrile or placebo.

The subjects enrolled in this study undergo repeated CPX and echocardiograms over the first 12 months of the trial.

Study Endpoints:

The primary clinical activity endpoints are:
A reduction and/or absence of any of the following: pericarditic chest pain, pericardial friction rubs, widespread ST-segment elevation, and/or PR depressions not reported previously, and new or worsening pericardial effusion, recurrent pain, fever, pericardial friction rub, ECG changes, echocardiographic evidence of pericardial effusion, and an elevation in the white blood cell count, erythrocyte sedimentation rate, or CRP.
A reduction and/or absence of any of the following:
symptoms within one week of therapy
recurrences
cardiac tamponade
constrictive pericarditis

Example 18. Treatment of Cardiac Allograft Rejection with Dapansutrile in Rats (Prophetic Example)

Objectives:

To investigate the efficacy of dapansutrile, formulated as a capsule for oral administration to rats, in treating, reducing the side-effects, and/or improving outcomes of rats who are experiencing or who have had cardiac allograft rejection.

Formulation:

The formulation used in this example is a capsule containing a blend of dapansutrile and Avicel® PH-101. Each placebo capsule contains only Avicel® PH-101. Both the dapansutrile capsules and the placebo capsules are formulated for oral administration and dosages are determined based on weights of each mouse.

Methodology:

Heterotopic vascularized intra-abdominal cardiac transplantation is performed suing a modification of a technique originally described by Ono and Lindsey (Ono, K, and Lindsey, E. S. Improved technique of heart transplantation in rats. *J. Thorac. Cardiovasc. Surg.* 57:225, 1969) Grafts are evaluated daily for heartbeat by abdominal palpation. Rejection is determined by the absence of palpable contractions in the transplanted organ. Following excision, heart tissue is prepared for histology using suitable techniques, and/or for other suitable methods of analysis. Rats from each of the four different groups (placebo and no transplant, placebo with transplant, dapansutrile with no transplant, and dapansutrile with transplant) are sacrificed at various timepoints and several factors with respect to the rat's physiology are analyzed. These factors are compare to one or more controls, including but not limited to, the placebo groups.

Study Endpoints:
hsCRP
IL-1β
IL-6
CPX
Allograft acceptance according to days (or months or years) of graft survival
Reduced inflammation
Lack of re-hospitalization

Example 19. Treatment of Heart Failure with Dapansutrile (Prophetic Example)

Objectives:

To investigate the efficacy of dapansutrile, formulated as a capsule for oral administration to patients, in treating patients who are experiencing or who have experienced heart failure, such as NYHA II-III systolic heart failure.

Formulation:

The formulation used in this example is a capsule containing a blend of 100 mg of dapansutrile and Avicel® PH-101. Each placebo capsule contains only Avicel® PH-101. Both the dapansutrile capsules and the placebo capsules are formulated for oral administration.

Dose and Mode of Administration:

Dapansutrile capsules or Placebo Capsules are self-administered by mouth once or twice, depending on the Cohort, each day beginning at the Baseline visit and continuing through the planned Day 14 visit. The first dose of Investigational Product is administered while in the study clinic under supervision of site personnel.

Dose Selection:

The dose for Cohort 1 consists of five 100 mg dapansutrile capsules administered once a day (for a total of 500 mg of dapansutrile drug substance per day). The dose for Cohort 2 consists of five 100 mg dapansutrile capsules administered twice each day (BID, for a total of 1,000 mg of dapansutrile drug substance per day).

Concomitant Medication:

Concomitant medication use is recorded and reviewed at each study visit. Subjects remain on stable doses of allowed concomitant medications. Prohibited concomitant medications include oral corticosteroids (within two weeks prior to enrollment) or other immunomodulating therapies (within a period of five half-lives prior to enrollment). Subjects using or intending to use prohibited concomitant medications are excluded from enrollment in the study.

Methodology:

This is a randomized, double-blinded, single-center safety and pharmacodynamics study of sequential cohort, dose-escalating, repeat-dosing of dapansutrile or placebo (4:1 ratio) in subjects with stable systolic HF with LVEF<40% and symptomatic for NYHA functional classification II-III who show signs of systemic inflammation (high sensitivity plasma C reactive protein [hsCRP]>2 mg/L). A total of approximately 20 subjects are enrolled in 2 sequential cohorts by randomized allocation (8 active and 2 placebo within each cohort). Progression to cohort 2 with dose escalation occurs following the Day 28 visit of the last subject in the first cohort.

Subjects are screened and evaluated twice for eligibility: 1) at the time of Screening (up to 28 days prior to randomization); and 2) at the Baseline visit, prior to randomization. At Baseline, assessments are conducted and if the subject is eligible, the first dose of investigational product (either dapansutrile capsules or identical placebo capsules) is administered at the clinical site upon completion of all assessments and collection of baseline parameters. Subjects self-administer investigational product once or twice daily, depending on cohort, for up to fourteen (14) consecutive days beginning at the Baseline visit and continuing through the planned Day 14 visit. Subjects return to the study clinic on Days 4, 8, 14 and 28 for follow-up visits. Additionally, subjects are contacted for telephone follow-up on Day 42.

Safety and tolerability are evaluated by monitoring the occurrence of adverse events (AEs) and changes in abbreviated physical examination findings, vital signs and clinical safety laboratory test results (chemistry, hematology and cardiac biomarkers) and body composition measured by bio-impedance analysis. Pharmacodynamics/biomarker endpoints include blood sampling for plasma hsCRP, IL-1β and interleukin-6 (IL-6), among others. Assessment of cardiorespiratory fitness include measurement of peak oxygen consumption (peak $VO_2$), and ventilatory efficiency (VE/$VCO_2$ slope) using cardiopulmonary exercise testing (CPX).

Cardiac systolic and diastolic function are measured with transthoracic Doppler echocardiography and quality of life questionnaires (Kansas City Cardiomyopathy Questionnaire and Duke Activity Status Index). Additionally, blood samples are collected for pharmacokinetic assessment of dapansutrile exposure.

Approximately ten (10) subjects are randomized in the first cohort with replacement allowed for subjects who discontinue before Day 14. Upon completion of the Day 28 visit by all subjects in Cohort 1, an interim data analysis is conducted and reviewed by the Medical Monitor, an independent cardiologist and the Principal Investigator and a decision about the progression of the study to enroll Cohort 2 will be made.

Inclusion Criteria (can include one or more of the following, but is not limited to the following):
 Male and female subjects 18 years old or older.
 Symptomatic stable HF (NYHA class with reduced left ventricular ejection fraction (LVEF≤40%, measured within 6 months of enrollment—no changes in cardiac medications or new device implantation within past 2 months).
 Peak exercise limited by shortness of breath and associated with a respiratory exchange ratio (RER) >1.00 (reflecting maximal aerobic effort)
 Reduced peak aerobic exercise capacity (peak VO2) to less than 80% of predicted value by age/gender at Baseline.
 Plasma hsCRP levels >2 mg/L at Screening.
 Acceptable overall medical condition to be safely enrolled in and to complete the study (with specific regard to cardiovascular, renal and hepatic conditions) in the opinion of the Principal Investigator.
 Ability to provide written, informed consent prior to initiation of any study-related procedures, and ability, in the opinion of the Principal Investigator, to understand and comply with all the requirements of the study.

Exclusion Criteria (can include one or more of the following, but is not limited to the following):
 Pregnant, nursing or intent to become pregnant during the study
 Abnormal blood pressure or heart rate response, angina or ECG changes (ischemia or arrhythmias) occurring during CPX
 Presence or known history of autoimmune conditions (e.g., systemic lupus erythematosus, hypophysitis, etc.)
 History or evidence of active tuberculosis (TB) infection at Baseline visit or one of the risk factors for tuberculosis such as but not limited or exclusive to:
  History of any of the following: residence in a congregate setting (e.g., jail or prison, homeless shelter, or chronic care facility), substance abuse (e.g., injection or non-injection), health-care workers with unprotected exposure to subjects who are at high risk of TB or subjects with TB disease before the identification and correct airborne precautions of the subject, or
  Close contact (i.e., share the same air space in a household or other enclosed environment for a prolonged period (days or weeks, not minutes or hours)) with a person with active pulmonary TB disease within the last 12 months.
 Use of any prohibited concomitant medications/therapies or planned use of any prohibited concomitant medications/therapies during the Treatment Period
 Any other concomitant medical or psychiatric condition(s), disease(s) or prior surgery(ies) that, in the opinion of the Principal Investigator, would impair the subject from safely participating in the trial and/or completing protocol requirements, including but not limited to:
 physical inability to walk or run on a treadmill
 decompensated HF (edema, NYHA IV)
 significant ischemic heart disease, angina
 arterial hypotension (blood pressure [BP] systolic <90 mmHg)
 arterial hypertension (resting BP systolic >160 mmHg)
 atrial fibrillation with rapid ventricular response
 severe valvular disease
 severe chronic obstructive or restrictive pulmonary disease
 moderate-severe anemia (Hgb<10 g/dL)
 severe diabetic neuropathy or myopathy
 Active or recent (within 2 weeks) infection prior to the Baseline visit
 History of or known positive for HIV, Hepatitis B surface antigen or antibodies to Hepatitis C Virus
 Active malignancy or recent malignancy with chemotherapy treatment within the past 6 months
 Enrollment in any trial and/or use of any investigational product or device within the immediate 30-day period prior to the Baseline visit
 Previous exposure to the investigational product Criteria for Evaluation (can Include One or More of the Following, but is not Limited to the Following):

The trial duration is approximately 42 days for all subjects randomized, which will consist of 6 visits to the study site: Screening (up to 28 days prior to Baseline), Baseline (Day 1), Day 4 (±1 day), Day 8 (±2 days), Day 14 (±2 days) and Day 28 (±2 days). Additionally, subjects are contacted for telephone follow-up on Day 42 (±3 days).

Safety Criteria:
 Physical examination (abbreviated general and site-specific examination)
 Vital Signs (pulse, resting blood pressure, temperature, respiration rate)
 Safety laboratory measures (chemistry, hematology and cardiac biomarkers)
 Bio-impedance analysis
 Cardiopulmonary exercise test
 Transthoracic Doppler echocardiography
 Plasma NT-proBNP levels
 Adverse events during the clinical trial Pharmacodynamics Outcomes: Blood samples will be collected at each study visit for PD/biomarker analysis, including:
 Levels of hsCRP
 Levels of circulating cytokines (e.g., IL-1β, IL-6)

Pharmacokinetic outcomes include, but are not limited to, determining plasma concentrations of dapansutrile.

Quality of life outcomes are assessed by the Kansas City Cardiomyopathy Questionnaire and Duke Activity Status Index to measure changes in symptoms.

Study Endpoints:
The primary clinical activity endpoints are:
 The patient's pharmacodynamics/biomarker endpoints will include blood sampling for plasma hsCRP, IL-1β and interleukin-6 (IL-6), B-type Natriuretic Peptide (BNP), among others, following the 28 day study
 Improvement in patient's CPX score(s), ECG, and/or bioimpedance analysis
 Whether the patient has been re-hospitalized The secondary clinical activity endpoints include the patient's single and multiple-dose pharmacokinetic profiles.

Example 20. Treatment of Stroke with Dapansutrile (Prophetic Example)

Objectives:
To investigate the efficacy of dapansutrile, formulated as a capsule for oral administration to patients, in treating and/or improving outcomes of patients who are experiencing or who have experienced one or more strokes.

Formulation:
The formulation used in this example is a capsule containing a blend of 100 mg of dapansutrile and Avicel® PH-101. Each placebo capsule contains only Avicel® PH-101. Both the dapansutrile capsules and the placebo capsules are formulated for oral administration.

Methodology:
A randomized, double-blind, placebo controlled, parallel treatment clinical activity study.

Patients with anterior cerebral circulation occlusion and onset of stroke that exceeds 4.5 hours but lasts less than 48 hours are randomly divided into two groups, including (1) standard management and placebo, (2) standard management plus dapansutrile (100 mg per day orally for 14 consecutive days, or (3) standard management plus dapansutrile (200 mg per day orally for 14 consecutive days. Administration of the placebo or either dose of dapansutrile begins within one hour after the baseline MRI and no later than 48 hours after the onset of symptoms.

Patients are monitored for adverse events and neurological outcomes up to 28 days from onset of treatment. Data are reviewed in an ongoing fashion by a data safety monitoring board (DSMB). Dose escalation is continuous unless drug-related toxicity reaches a predetermined level of one dose-limiting adverse event (1 of 4 treated) within a dose cohort, in which case a second cohort of 5 patients (4:1) is treated at that dose. The study is terminated at a dose level at which 2 of 4 or 3 of 8 patients on active treatment have a severe dose limiting toxicity or when all planned dose cohorts have been completed.

Inclusion Criteria (can include one or more of the following, but is not limited to the following):
>18 years of age
Anterior-circulation ischemic stroke
   All patients with symptoms of focal neurological deficits and simultaneous radiological evidence (magnetic resonance imaging, MRI) of an ischemic brain lesion
measurable neurological deficit (NIHSS>5)
interval between symptom onset and admission more than 4.5 hours and less than 48 hours
   All patients are recruited beyond the 4.5 hours of symptom onset and are past the accepted time-window for thrombolytic therapy
Exclusion Criteria (can include one or more of the following, but is not limited to the following):
hemorrhagic stroke and severe hemorrhage in other organs
other diseases of the central nervous system (CNS)
diabetes mellitus
tumor or hematological systemic diseases
any infection before acute ischemic stroke
concomitant use of antineoplastic or immune modulating therapies
contraindication to MRI Criteria for Evaluation (can Include One or More of the Following, but is not Limited to the Following):
Study Endpoints:
The primary clinical activity endpoint is:
Changes in lesion volume [Time Frame: lesion volume from baseline to day 7]
brain inflammatory level (BMS) [Time Frame: day 7]
extent of clinical improvement [Time Frame: from baseline to day 7 and 14]
The secondary clinical activity endpoints are:
probability of excellent recovery [Time Frame: at day 90] as defined as a score of 0 or 1 on the mRS
cytotoxic edema [Time Frame: day 3] (ADC value)

Example 21. Treatment of Peripheral Vascular Disease with Dapansutrile (Prophetic Example)

Objectives:
To investigate the efficacy of dapansutrile, formulated as a capsule for oral administration to patients, in treating, reducing the side-effects, and/or improving outcomes of patients who are experiencing or who have had peripheral vascular disease. In particular, the study is designed to assess the safety, tolerability and efficacy of dapansutrile on the leg artery structure and physical activity in patients with atherosclerotic peripheral artery disease and leg pain from walking.

Formulation:
The formulation used in this example is a capsule containing a blend of 100 mg of dapansutrile and Avicel® PH-101. Each placebo capsule contains only Avicel® PH-101. Both the dapansutrile capsules and the placebo capsules are formulated for oral administration.

Methodology:
A multicenter, randomized, double-blind, placebo-controlled study of the safety, tolerability and effects on arterial structure and function of dapansutrile in patients with intermittent claudication.

Inclusion Criteria (can include one or more of the following, but is not limited to the following):
Signed informed consent form
Between the ages of 18 and 85
Experiences leg pain associated with walking and have an ankle brachial index between 0.40 and 0.9
On stable aspirin and statin doses for at least 6 weeks
Blood pressure within ranges specified in the protocol
Able to communicate well and understand and comply with the study procedures
Exclusion Criteria (can include one or more of the following, but is not limited to the following):
Recent use of any other experimental drugs
Pregnant or nursing women
Women of child bearing potential unless willing to use contraception as detailed in the protocol
Cannot walk 15 meters (50 feet)
People on restricted medications as listed in the protocol
Any open or non-healing wounds with 3 months of study start or infection within 2 weeks or study start
Significant heart disease
Uncontrolled diabetes
Significant kidney or liver disease
Live vaccinations within 3 months of study start
History of untreated tuberculosis or active tuberculosis (TB)
Patients with metal in their body (excluded due to MRI scan) as detailed in the protocol.

Criteria for Evaluation (can Include One or More of the Following, but is not Limited to the Following):
Study Endpoints:
The primary clinical activity endpoint is:
Mean Vessel Wall Area Ratio of 12 Months to Baseline [Time Frame: Baseline, 12 months post-dose]
Peripheral artery wall area (superficial femoral artery) measured using Magnetic Resonance Imaging (MRI) cross-section slices.
Mean vessel wall area ($mm^2$) is derived by converting total plaque volume (TPV) (mL) of the vessel to $mm^3$ by multiplying by 1000, dividing by the number of slices used for the volume calculation, and dividing by the thickness of a slice (3 mm). Least squares mean for ratio of 12 months to baseline is measured from repeated measures mixed effect model with visit, treatment, the treatment-by-visit interaction, baseline and the visit-by-baseline interaction as fixed effects The secondary clinical activity endpoints are:
Number of patients with adverse events in 12 months [Time Frame: Baseline to 12 months post-dose]
Summary statistics on adverse event is reported. It is categorized as number of patients in total adverse events (non serious and serious AEs), serious adverse event, death.
Serum Amyloid A (SAA) level ratio of 12 months to baseline [Time Frame: Baseline, 12 months post-dose]
Least squares mean for ratio of 12 months to baseline is measured from repeated measures mixed effect model with visit, treatment, treatment-by-visit interaction, baseline and the visit-by-baseline interaction as fixed effects.
hsCRP Ratio of 12 Months to Baseline [Time Frame: Baseline, 12 months post-dose]
Least squares mean for ratio of 12 months to baseline is measured from repeated measures mixed effect model with visit, treatment, treatment-by-visit interaction, baseline and the visit-by-baseline interaction as fixed effects.

It is to be understood that the foregoing describes preferred embodiments of the present invention and that modifications may be made therein without departing from the scope of the present invention as set forth in the claims.

What is claimed is:

1. A method of treating acute myocardial infarction (AMI) in a subject, comprising the step of:
   administering to the subject suffering from AMI an effective amount of 3-methanesulfonylpropionitrile.
2. The method according to claim 1, wherein said compound is administered by systemic administration.
3. The method according to claim 2, wherein said compound is administered by oral administration.
4. The method according to claim 1, wherein the treated subject has a reduction in area of damaged cardiac tissue, or infarct size.
5. The method according to claim 1, wherein the AMI is ischemia AMI, reperfusion AMI, or non-reperfusion AMI.
6. The method according to claim 3, wherein the subject is a human subject, and the dosage is 1-50 mg/kg/day.
7. The method according to claim 3, wherein the subject is a human subject, and the dosage is 5-50 mg/kg/day.

* * * * *